United States Patent
Inomata

(10) Patent No.: US 11,351,761 B2
(45) Date of Patent: Jun. 7, 2022

(54) COMPOSITION FOR LAMINATED MATERIAL USED FOR MEDICAL LUBRICATING MEMBER, LAMINATED MATERIAL USED FOR MEDICAL LUBRICATING MEMBER, MEDICAL LUBRICATING MEMBER, AND MEDICAL DEVICE

(71) Applicant: FUJIFILM Corporation, Tokyo (JP)

(72) Inventor: Sotaro Inomata, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/147,679

(22) Filed: Jan. 13, 2021

(65) Prior Publication Data

US 2021/0129511 A1 May 6, 2021

Related U.S. Application Data

(63) Continuation of application No. PCT/JP2019/028027, filed on Jul. 17, 2019.

(30) Foreign Application Priority Data

Jul. 17, 2018 (JP) .............................. JP2018-134502

(51) Int. Cl.
*B32B 27/28* (2006.01)
*B32B 27/08* (2006.01)
(Continued)

(52) U.S. Cl.
CPC ............ *B32B 27/283* (2013.01); *B32B 27/08* (2013.01); *B32B 27/26* (2013.01); *B32B 27/308* (2013.01);
(Continued)

(58) Field of Classification Search
CPC ....... B32B 27/283; B32B 27/08; B32B 27/26; B32B 27/308; B32B 27/322; B32B 27/40;
(Continued)

(56) References Cited

U.S. PATENT DOCUMENTS

| 5,997,517 A | 12/1999 | Whitbourne |
| 2002/0107330 A1 | 8/2002 | Pinchuk et al. |

(Continued)

FOREIGN PATENT DOCUMENTS

| CN | 1250382 A | 4/2000 |
| CN | 1299382 A | 6/2001 |

(Continued)

OTHER PUBLICATIONS

Machine translation of JP2005-74139 (Year: 2005).*

(Continued)

*Primary Examiner* — Michael C Miggins
(74) *Attorney, Agent, or Firm* — Sughrue Mion, PLLC

(57) ABSTRACT

There is provided a composition for a laminated material used for a medical lubricating member, the composition including a polymer b1 including a polysiloxane structure and a crosslinkable polymer b2 having a particular reactive group that forms a crosslinked body with the polymer b1 and having a number-average molecular weight of 1000 or more. The crosslinkable polymer b2 is at least one of polysaccharides, polyethyleneimines, polyesters, polyethers, polyamides, polyurethanes, polyureas, or polyimides. There are also provided a laminated material used for a medical lubricating member and including the composition, a medical lubricating member, and a medical device.

13 Claims, 1 Drawing Sheet

(51) Int. Cl.
  *B32B 27/26* (2006.01)
  *B32B 27/30* (2006.01)
  *B32B 27/32* (2006.01)
  *B32B 27/40* (2006.01)

(52) U.S. Cl.
  CPC ............ *B32B 27/322* (2013.01); *B32B 27/40* (2013.01); *B32B 2250/02* (2013.01); *B32B 2250/03* (2013.01); *B32B 2250/24* (2013.01); *B32B 2307/728* (2013.01); *B32B 2307/746* (2013.01); *B32B 2535/00* (2013.01)

(58) Field of Classification Search
  CPC . B32B 2250/02; B32B 2250/03; C08G 64/18; C08G 77/445; C08G 77/448; C08G 61/00; C08G 61/02; C08G 81/00
  See application file for complete search history.

(56) References Cited

U.S. PATENT DOCUMENTS

| | | |
|---|---|---|
| 2002/0128419 A1 | 9/2002 | Terry et al. |
| 2003/0018156 A1 | 1/2003 | Meijs et al. |
| 2009/0104095 A1 | 4/2009 | Morgan et al. |
| 2012/0026457 A1 | 2/2012 | Qiu et al. |
| 2015/0203716 A1 | 7/2015 | Moravek et al. |
| 2017/0204213 A1 | 7/2017 | Kato et al. |
| 2019/0328931 A1 | 10/2019 | Inomata et al. |

FOREIGN PATENT DOCUMENTS

| | | |
|---|---|---|
| CN | 101934101 A | 1/2011 |
| CN | 103038699 A | 4/2013 |
| CN | 105983137 A | 10/2016 |
| JP | 2000-248045 A | 9/2000 |
| JP | 2005-74139 A | 3/2005 |
| JP | 2006-235269 A | 9/2006 |
| JP | 2008-289864 A | 12/2008 |
| JP | 2011-500500 A | 1/2011 |
| JP | 2014-105325 A | 6/2014 |
| WO | 2015/198919 A1 | 12/2015 |
| WO | 2018131518 A1 | 7/2018 |

OTHER PUBLICATIONS

International Search Report dated Sep. 17, 2019 from the International Searching Authority in International Application No. PCT/JP2019/028027.
Written Opinion dated Sep. 17, 2019 from the International Bureau in International Application No. PCT/JP2019/028027.
International Preliminary Report on Patentability dated Jan. 17, 2021 (global dossier date) from the International Bureau in International Application No. PCT/JP2019/028027.
Extended European Search Report dated Aug. 23, 2021 from the European Patent Office in EP Application No. 19838185.7.
Office Action dated Aug. 3, 2021 in Japanese Application No. 2020-531330.
Communication dated Nov. 25, 2021, issued by the State Intellectual Property Office of the P.R.C. in corresponding application No. 201980043115.X.

* cited by examiner

COMPOSITION FOR LAMINATED MATERIAL USED FOR MEDICAL LUBRICATING MEMBER, LAMINATED MATERIAL USED FOR MEDICAL LUBRICATING MEMBER, MEDICAL LUBRICATING MEMBER, AND MEDICAL DEVICE

CROSS-REFERENCE TO RELATED APPLICATIONS

This application is a Continuation of PCT International Application No. PCT/JP2019/028027 filed on Jul. 17, 2019, which claims priority under 35 U.S.C. § 119 (a) to Japanese Patent Application No. 2018-134502 filed in Japan on Jul. 17, 2018. Each of the above applications is hereby expressly incorporated by reference, in its entirety, into the present application.

BACKGROUND OF THE INVENTION

1. Field of the Invention

The present invention relates to a composition for laminated materials used for medical lubricating members, a laminated material used for medical lubricating members, a medical lubricating member, and a medical device.

2. Description of the Related Art

Medical devices that are inserted into or applied to blood vessels, the trachea, the digestive tract, or other body cavities or tissues in order to examine or treat a human body are required not to cause tissue damage or inflammation upon contact with the tissue.

A material including a silicone component is disclosed as a material for such a medical device. For example, JP2008-289864A describes an antithrombotic material including a (meth)acrylate copolymer formed of a hydrophobic (meth)acrylate and a hydrophilic (meth)acrylate. JP2008-289864A describes that the hydrophobic (meth)acrylate is at least one of silicone (meth)acrylate or alkyl (meth)acrylate and that the (meth)acrylate copolymer is insoluble in water and viscous liquid at room temperature.

WO15/198919A describes a silicone hydrogel that has a repeating unit derived from a monofunctional linear silicone (meth)acrylate and a repeating unit derived from a hydrophilic (meth)acrylate, the content of the repeating units derived from the (meth)acrylates being more than 80 mass %, and that further includes a repeating unit derived from a polyfunctional monomer having two or more polymerizable groups, such as tetramethylene glycol dimethacrylate. This silicone hydrogel can be suitably used for various medical tools having a good balance of modulus of elasticity, wettability, and transparency, in particular, for ophthalmic lenses such as contact lenses.

SUMMARY OF THE INVENTION

When a medical device is used in contact with a body tissue, high friction between the medical device and a surface of the tissue damages the tissue. For example, an endoscope is used by being slid in a body cavity, and therefore it is important to improve the slidability of a surface member that comes into contact with a tissue in a body cavity. Since the inside of the body cavity is in a wet state, the surface member of the medical device (endoscope) is required to have high slidability particularly in a wet state.

In some cases, a medical tube is inserted into a body cavity, and a camera, a jig, and the like are inserted into the tube while water is being passed through the tube to observe the inside of the body cavity or to take a biopsy. In this case, it is required to improve the slidability between the inner wall of the tube and the camera, the jig, and the like in a wet state. In order to improve the slidability required for the endoscope, the medical tube, and the like, a medical lubricating member having a hydrophilic lubricating coating layer has been studied as a surface member. The medical lubricating member has a structure in which an undercoat layer and a hydrophilic lubricating coating layer are disposed in this order on a substrate. The undercoat layer of the medical lubricating member having this structure functions as an adhesive between the substrate and the hydrophilic lubricating coating layer.

As a result of studies conducted by the present inventors, it has been found that the adhesiveness between the substrate and the undercoat layer on the substrate may decrease over time during storage of the medical lubricating member having the above structure. From the viewpoint of ensuring the quality, effectiveness, and safety of medical devices, a medical lubricating member used for medical devices is desired to have a long service life. Since the adhesiveness between the substrate and the undercoat layer on the substrate affects the service life of the medical lubricating member, it is required that excellent adhesiveness can be maintained even after the passage of time.

Accordingly, it is an object of the present invention to provide a composition and a laminated material capable of providing a medical lubricating member which has excellent adhesiveness between a substrate and a layer disposed on the substrate and whose adhesiveness can be maintained at a desired high level for a long time. It is another object of the present invention to provide a medical lubricating member which has excellent adhesiveness between a substrate and a layer disposed on the substrate and whose adhesiveness can be maintained at a desired high level for a long time. It is still another object of the present invention to provide a medical device including the above medical lubricating member.

As a result of thorough studies conducted by the present inventors in view of the foregoing objects, it has been found that the above-mentioned decrease in adhesiveness over time during storage of the medical lubricating member is caused by plasticization of the layer due to, for example, bleed-out of low-molecular-weight components in the substrate to the surface of the substrate and adsorption of carbon dioxide in the air. As a result of further studies conducted by the present inventors, it has been found that by using a crosslinked body formed from a polymer including a polysiloxane structure and a particular crosslinkable polymer having a negative element in the main chain as a component constituting a layer disposed on a substrate, the medical lubricating member is less susceptible to the plasticization due to, for example, the bleed-out and the adsorption of carbon dioxide. Thus, the adhesiveness between the substrate and the layer disposed on the substrate can be maintained at a desired high level even after the passage of time.

Further studies have been conducted based on these findings, and the present invention has been completed.

The above objects of the present invention have been achieved by the following means.

<1>

A composition for a laminated material used for a medical lubricating member includes a polymer b1 including a polysiloxane structure and a crosslinkable polymer b2 having a reactive group that forms a crosslinked body with the polymer b1.

The reactive group is at least one reactive group in Group I of reactive groups.

The crosslinkable polymer b2 is at least one of polysaccharides, polyethyleneimines, polyesters, polyethers, polyamides, polyurethanes, polyureas, or polyimides.

The crosslinkable polymer b2 has a number-average molecular weight of 1000 or more.

Group I of Reactive Groups hydroxy group, carboxy group, amino group, isocyanate group, oxazolinyl group, epoxy group, vinyl group, ethynyl group, sulfanyl group, azide group, trialkoxysilyl group, halogenated methyl group, and acid anhydride structure

<2>

A laminated material used for a medical lubricating member includes a substrate a and a layer b disposed on the substrate a.

The layer b is a layer including a crosslinked body formed from a polymer b1 including a polysiloxane structure and a crosslinkable polymer b2 having at least one reactive group in Group I of Reactive Groups.

The crosslinkable polymer b2 is at least one of polysaccharides, polyethyleneimines, polyesters, polyethers, polyamides, polyurethanes, polyureas, or polyimides.

The crosslinkable polymer b2 has a number-average molecular weight of 1000 or more.

Group I of Reactive Groups hydroxy group, carboxy group, amino group, isocyanate group, oxazolinyl group, epoxy group, vinyl group, ethynyl group, sulfanyl group, azide group, trialkoxysilyl group, halogenated methyl group, and acid anhydride structure

<3>

In the laminated material used for a medical lubricating member according to <2>, the polymer b1 is a graft polymer having the polysiloxane structure in a graft chain.

<4>

In the laminated material used for a medical lubricating member according to <2> or <3>, the polymer b1 has a structural unit represented by formula (1) below and has at least one of a structural unit represented by formula (2) below, a structural unit represented by formula (3) below, or a structural unit represented by formula (4) below.

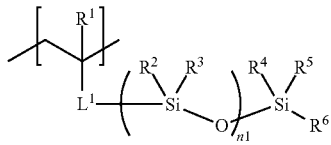

Formula (1)

In the formula, $R^1$ to $R^6$ represent a hydrogen atom or an organic group. L represents a single bond or a divalent linking group, and n1 represents 3 to 10000.

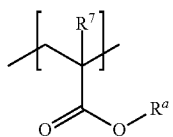

Formula (2)

In the formula, $R^7$ and $R^a$ represent a hydrogen atom or an organic group.

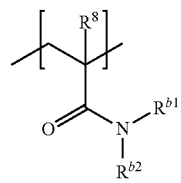

Formula (3)

In the formula, $R^8$, $R^{b1}$, and $R^{b2}$ represent a hydrogen atom or an organic group.

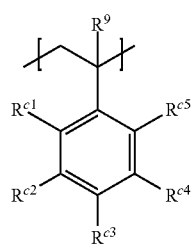

Formula (4)

In the formula, $R^9$ represents a hydrogen atom or an organic group. $R^{c1}$ to $R^{c5}$ represent a hydrogen atom, a halogen atom, or an organic group.

<5>

In the laminated material used for a medical lubricating member according to <4>, $R^a$ represents a group represented by formula (5) below or a nitrogen-containing organic group.

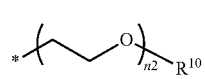

Formula (5)

In the formula, n2 represents 1 to 10000. $R^{10}$ represents a hydrogen atom or an organic group. * represents a bonding site.

<6>

In the laminated material used for a medical lubricating member according to <4> or <5>, n1 represents 135 to 10000.

<7>

In the laminated material used for a medical lubricating member according to any one of <2> to <6>, the crosslinkable polymer b2 is at least one of polysaccharides, polyethyleneimines, polyesters, polyethers, polyamides, or polyurethanes.

<8>

In the laminated material used for a medical lubricating member according to any one of <2> to <7>, a content of a constituent component derived from the crosslinkable polymer b2 in the crosslinked body is 30 to 90 mass %.

<9>

In the laminated material used for a medical lubricating member according to any one of <2> to <8>, the layer b has a surface subjected to hydrophilic treatment.

<10>

In the laminated material used for a medical lubricating member according to any one of <2> to <9>, the substrate a is formed of at least one of a urethane resin, a silicone resin, a fluorocarbon resin, an olefin resin, or an acrylic resin.

<11>

In the laminated material used for a medical lubricating member according to any one of <2> to <10>, the substrate a is formed of a silicone resin.

<12>

In the laminated material used for a medical lubricating member according to any one of <2> to <11>, the medical lubricating member is used as a member of a medical device selected from the group consisting of a medical tube, a guide wire, an endoscope, a surgical needle, a surgical suture, forceps, an artificial blood vessel, an artificial heart, and a contact lens.

<13>

A medical lubricating member has the laminated material used for a medical lubricating member according to any one of <2> to <12> and a layer c that is disposed on the layer b constituting the laminated material and that includes a hydrophilic polymer.

<14>

A medical device includes the medical lubricating member according to <13>, wherein the medical device is selected from the group consisting of a medical tube, a guide wire, an endoscope, a surgical needle, a surgical suture, forceps, an artificial blood vessel, an artificial heart, and a contact lens.

In this specification, every numerical range expressed using "to" means a range including numerical values before and after "to" as the lower and upper limits.

In this specification, when a plurality of substituents and linking groups are represented by a particular symbol (hereafter referred to as substituents and the like) or when a plurality of substituents and the like are simultaneously or alternatively defined, the substituents and the like may be the same as or different from each other. The same also applies to the definition of the number of substituents and the like. When a plurality of substituents and the like are close (particularly adjacent) to each other, they may be linked or fused to each other to form a ring. In a polymer having a plurality of structural units having a substituent or a linking group represented by a particular symbol, the plurality of structural units may be the same as or different from each other.

In this specification, unless otherwise specified, the form of polymers is not particularly limited, and may be any form such as random, block, or graft as long as the effects of the present invention are not impaired.

In this specification, the terminal structure of polymers is not particularly limited. The terminal structure is appropriately determined in accordance with the type of substrate used during synthesis, the type of quenching agent (reaction terminator) during synthesis, and the like, and is not uniquely determined. Examples of the terminal structure include a hydrogen atom, a hydroxy group, a halogen atom, an ethylenically unsaturated group, and an alkyl group.

In this specification, the terms "acrylic acid", "acrylamide", and "styrene" are used in a broader sense than usual.

That is, the term "acrylic acid" refers to all compounds having a structure of $R^A$—$C(=CR^B{}_2)COOH$ ($R^A$ and $R^B$ each independently represent a hydrogen atom or a substituent). The term "acrylamide" refers to all compounds having a structure of $R^C$—$C(=CR^D{}_2)CONR^E{}_2$ ($R^C$, $R^D$, and $R^E$ each independently represent a hydrogen atom or a substituent).

The term "styrene" refers to all compounds having a structure of $R^F$—$C(=CR^G{}_2)C_6R^H{}_6$ ($R^F$, $R^G$, and $R^H$ each independently represent a hydrogen atom or a substituent).

In this specification, when the number of carbon atoms of a certain group is specified, the number of carbon atoms means the number of carbon atoms of the entire group. That is, in the case where the group further has a substituent, the number of carbon atoms means the total number of carbon atoms of the group including the substituent.

In this specification, the weight-average molecular weight (Mw) and the number-average molecular weight (Mn) can be measured as molecular weights in terms of polystyrene by gel permeation chromatography (GPC) unless otherwise specified. At this time, the GPC instrument is HLC-8220 (manufactured by Tosoh Corporation), the column is G3000HXL+G2000HXL (both are TSK-gel HXL (trade name) series manufactured by Tosoh Corporation), the flow rate is 1 mL/min at 23° C., and detection is performed by using refractive index (RI). The eluant can be selected from the group consisting of THF (tetrahydrofuran), chloroform, NMP (N-methyl-2-pyrrolidone), and m-cresol/chloroform (manufactured by Shonan Wako Pure Chemical Industries, Ltd.), and THF is used as long as the target material is dissolved in THF.

In the measurement of the molecular weight of a polymer used in a hydrophilic coating layer, N-methyl-2-pyrrolidone (manufactured by Wako Pure Chemical Industries, Ltd.) is used as an eluant, and TSK-gel Super AWM-H (trade name) manufactured by Tosoh Corporation is used as a column.

The medical lubricating member or the medical device according to an embodiment of the present invention is excellent in terms of adhesiveness between a substrate and a layer disposed on the substrate that constitute the medical lubricating member, and the adhesiveness can be maintained at a desired high level for a long time. The composition for a laminated material used for a medical lubricating member and the laminated material according to embodiments of the present invention can provide a medical lubricating member according to an embodiment of the present invention.

DESCRIPTION OF THE PREFERRED EMBODIMENTS

Figure 1:
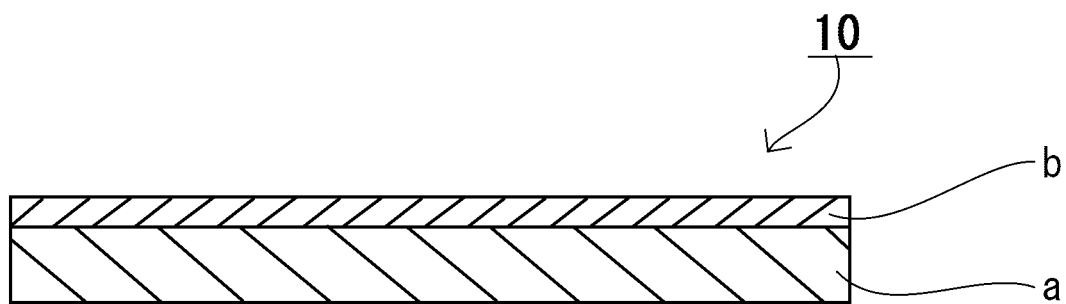
FIG. 1 is a longitudinal sectional view illustrating a laminated material used for a medical lubricating member according to an embodiment of the present invention.

The composition for a laminated material used for a medical lubricating member according to an embodiment of the present invention (hereafter also referred to as a "composition according to an embodiment of the present invention") includes a polymer b1 including a polysiloxane structure and a crosslinkable polymer b2, and can be suitably used for forming a laminated material used for the medical lubricating member according to an embodiment of the present invention (hereafter also referred to as a "laminated material according to an embodiment of the present invention").

Composition According to Embodiment of the Present Invention

The composition according to an embodiment of the present invention includes a polymer b1 including a polysiloxane structure and a crosslinkable polymer b2.

The crosslinkable polymer b2 is at least one of polysaccharides, polyethyleneimines, polyesters, polyethers, polyamides, polyurethanes, polyureas, and polyimides each having at least one reactive group in Group I of reactive groups below. The crosslinkable polymer b2 has a number-average molecular weight of 1000 or more. Through the reactive group of the crosslinkable polymer b2, the crosslinkable polymer b2 can form a crosslinked body with the polymer b1 including a polysiloxane structure. For the polymer b1 including a polysiloxane structure and the crosslinkable polymer b2, a polymer b1 including a polysiloxane structure and a crosslinkable polymer b2 in a laminated material according to an embodiment of the present invention described later can be preferably used.

Group I of Reactive Groups hydroxy group, carboxy group, amino group, isocyanate group, oxazolinyl group, epoxy group, vinyl group, ethynyl group, sulfanyl group, azide group, trialkoxysilyl group, halogenated methyl group, and acid anhydride structure The composition according to an embodiment of the present invention may include a solvent.

Examples of the solvent that can be included in the composition according to an embodiment of the present invention include ether solvents such as dibutyl ether, dimethoxymethane, dimethoxyethane, diethoxyethane, propylene oxide, 1,4-dioxane, 1,3-dioxolane, 1,3,5-trioxane, tetrahydrofuran, anisole, and phenetole; ketone solvents such as acetone, methyl ethyl ketone, diethyl ketone, dipropyl ketone, diisobutyl ketone, methyl isobutyl ketone, cyclopentanone, cyclohexanone, methylcyclohexanone, and dimethylcyclohexanone; ester solvents such as ethyl formate, propyl formate, n-pentyl formate, methyl acetate, ethyl acetate, methyl propionate, ethyl propionate, n-pentyl acetate, and γ-butyrolactone; alcohol solvents such as methanol, ethanol, 1-propanol, 2-propanol (isopropyl alcohol), 1-butanol, 2-butanol, tert-butanol, 1-pentanol, 2-methyl-2-butanol, and cyclohexanol; aromatic hydrocarbon solvents such as xylene and toluene; halogenated hydrocarbon solvents such as methylene chloride, chloroform, and 1,1-dichloroethane; amide-based solvents such as N-methyl-2-pyrrolidone (NMP), N,N-dimethylformamide (DMF), and N,N-dimethylacetamide (DMAc); nitrile solvents such as acetonitrile; and organic solvents having two or more functional groups, such as methyl 2-methoxyacetate, methyl 2-ethoxyacetate, ethyl 2-ethoxyacetate, ethyl 2-ethoxypropionate, 2-methoxyethanol, 2-propoxyethanol, 2-butoxyethanol, 1,2-diacetoxyacetone, acetylacetone, diacetone alcohol, methyl acetoacetate, N-methylpyrrolidone, propylene glycol monomethyl ether acetate, and ethyl acetoacetate.

When the composition according to an embodiment of the present invention includes a solvent, the content of the solvent in the composition is preferably 60 to 99 mass %, more preferably 70 to 99 mass %, and further preferably 80 to 99 mass %.

The solid content (content ratio) of components other than the solvent included in the composition according to an embodiment of the present invention is as described in the laminated material according to an embodiment of the present invention. The solid content of components other than the solvent refers to a content of components other than a solvent remaining in a laminated material when the laminated material according to an embodiment of the present invention is provided.

The composition according to an embodiment of the present invention is preferably stored at 20° C. to 40° C. with light shielding as necessary in order to suppress the progress of a crosslinking reaction due to formation of a covalent bond until use. Specifically, the term "until use" refers to, for example, until the composition is used for forming a laminated material used for a medical lubricating member.

Hereafter, preferred embodiments of the laminated material according to an embodiment of the present invention will be described.

Laminated Material According to Embodiment of the Present Invention

The laminated material according to an embodiment of the present invention is a material for forming a medical lubricating member according to an embodiment of the present invention described later. The laminated material according to an embodiment of the present invention is a laminated body having a substrate (hereafter also referred to as a "substrate a") and a layer (hereafter also referred to as a "layer b") disposed on the substrate a and including a crosslinked body formed from a polymer b including a polysiloxane structure described later and a crosslinkable polymer b2 having at least one reactive group in Group I of reactive groups above. The shape of the laminated body is not particularly limited. For example, the laminated material may have a flat surface as illustrated in FIG. 1 or may have a curved surface. The laminated material preferably has, for example, a tubular shape, and may have a spherical shape. From the viewpoint of producing the desired effects of the present invention, the layer b is directly disposed on the substrate a in the laminated material according to an embodiment of the present invention.

Substrate a

The material for the substrate a constituting the laminated material according to an embodiment of the present invention is not particularly limited. Materials that can be used for medical devices and the like can be widely employed. For example, glass, plastic, metal, ceramic, fiber, fabric, paper, leather, synthetic resin, and combinations thereof can be used in accordance with the purpose. Among them, plastic, ceramic, fiber, fabric, paper, leather, and synthetic resin may cause bleed-out of low-molecular-weight components. Therefore, even when the laminated material according to an embodiment of the present invention has a substrate a that is, at the interface with the layer b, formed of any of plastic, ceramic, fiber, fabric, paper, leather, and synthetic resin, plasticization of the layer b due to bleed-out of the low-molecular-weight components can be suppressed, and excellent adhesiveness can be maintained even after the passage of time. In particular, the substrate a is preferably formed of a resin. The shape of the substrate a is not particularly limited, and the substrate a may have, for example, a plate-like shape or a curved surface. The substrate a preferably has a tubular shape and may have a spherical shape.

The substrate a can be suitably used in the present invention even if a surface on which the layer b is to be formed has a low surface free energy. For example, the surface free energy of the surface of the substrate a on which the layer b is to be formed can be set in the range of 5 to 1500 mN/m and can also be set in the range of 10 to 500 mN/m. The surface free energy of the surface of the substrate a on which the layer b is to be formed may be 5 to 300 mN/m, 10 to 200 mN/m, or 10 to 100 mN/m and is also preferably 10 to 50 mN/m. Even when the surface free energy of the surface of the substrate a on which the layer b is to be formed is low, the layer b can be formed on the substrate a without causing cissing or unevenness because the crosslinked body in the layer b has a particular polymer b1 described later.

The surface free energy can be measured by a typical method. That is, the contact angle of a film is measured with both water and diiodomethane, and is substituted into the following Owens formula (the following is a formula in the case where diiodomethane ($CH_2I_2$) is used as an organic solvent).

$$1+\cos\theta_{H2O} = 2(\gamma_S^d)^{1/2}(\gamma_{H2O}^d)^{1/2}/\gamma_{H2O,V} + 2(\gamma_S^h)^{1/2}(\gamma_{H2O}^h)^{1/2}/\gamma_{H2O,V}$$

$$1+\cos\theta_{CH2I2} = 2(\gamma_S^d)^{1/2}(\gamma_{CH2I2}^d)^{1/2}/\gamma_{CH2I2,V} + 2(\gamma_S^h)^{1/2}(\gamma_{CH2I2}^h)^{1/2}/\gamma_{CH2I2,V} \quad \text{Owens formula}$$

Herein, $\gamma_{H2O}^d = 21.8$, $\gamma_{CH2I2}^d = 49.5$, $\gamma_{H2O}^h = 51.0$, $\gamma_{CH2I2}^h = 1.3$, $\gamma_{H2O,V} = 72.8$, and $\gamma_{CH2I2,V} = 50.8$. When the measured contact angle of water is substituted into $\theta_{H2O}$ and the measured contact angle of diiodomethane is substituted into $\theta_{CH2I2}$, the dispersion force component $\gamma_S^d$ and the polar component $\gamma_S^h$ of the surface energy are determined, respectively. The sum $\gamma_S^{Vh} = \gamma_S^d + \gamma_S^h$ can be determined as a surface free energy (mN/m).

The contact angle is measured by setting the droplet volume to 1 μL for both pure water and diiodomethane and reading the contact angle ten seconds after the dropping. At this time, the measurement atmosphere is set to a temperature of 23° C. and a relative humidity of 50%.

The material for the substrate a is, for example, suitably at least one of a urethane resin, a silicone resin, a fluorocarbon resin, an olefin resin, or an acrylic resin. From the viewpoint of use as a medical material and better adhesiveness that can be maintained over time, a silicone resin is more preferably used.

Urethane Resin

The urethane resin that can be used as a material for the substrate a is not particularly limited. In general, urethane resins are synthesized by addition polymerization of polyisocyanate and polyol. Examples of the urethane resins that can be used include aliphatic polyurethanes obtained by using an aliphatic isocyanate as a polyisocyanate raw material, aromatic polyurethanes obtained by using an aromatic isocyanate as a polyisocyanate raw material, and copolymers of such polyurethanes.

Furthermore, Pandex series (trade name, manufactured by DIC Corporation), V-Gran series, V-Top series, and DNT-urethane Smile Clean series (trade name, all manufactured by Dai Nippon Toryo Co., Ltd.) serving as urethane resin paints, Polyflex series (trade name, manufactured by DKS Co., Ltd.), Ti-Prene series (trade name, manufactured by Tigers Polymer Corporation), Tecoflex (registered trademark) series (Thermedics Inc.), Miractran series (trade name, manufactured by Nippon Miractran Company Limited), Pellethane series (trade name, manufactured by The Dow Chemical Company), and the like can also be used as the urethane resin.

Silicone Resin

The silicone resin that can be used as a material for the substrate a is not particularly limited, and the silicone resin may be cured using a curing agent. The curing reaction may be a typical reaction. For example, an organohydrogenpolysiloxane and an organopolysiloxane having an ethylenic C=C double bond can be cured using a platinum catalyst. In the case of curing the silicone resin by peroxide crosslinking, a peroxide is used.

Furthermore, rubber compound KE series (trade name, manufactured by Shin-Etsu Chemical Co., Ltd.), ELASTOSIL (registered trademark) series (manufactured by Wacker Asahikasei Silicone Co., Ltd.), SILASTIC (registered trademark) series (manufactured by Dow Corning Toray Co., Ltd.), TSE series (trade name, manufactured by Momentive Performance Materials Japan Co., Ltd.), and the like can be used as the silicone resin.

Fluorocarbon Resin

The fluorocarbon resin that can be used as a material for the substrate a is not particularly limited. For example, polytetrafluoroethylene, polyvinyl fluoride, polyvinylidene fluoride, polytrifluoroethylene, and copolymers thereof can be used.

Furthermore, Teflon (registered trademark, manufactured by DUPONT), Polyflon and Neoflon series (trade name, manufactured by Daikin Industries, Ltd.), Fluon (registered trademark) series and Cytop (registered trademark) series (manufactured by AGC Inc.), Dyneon series (trade name, manufactured by 3M), and the like can also be used as the fluorocarbon resin.

Olefin Resin

The olefin resin that can be used as a material for the substrate a is not particularly limited. For example, polyethylene, polypropylene, polybutene, polypentene, polycyclopentene, polymethylpentene, polystyrene, polybutadiene, polyisoprene, copolymers thereof, and natural rubber can be used. Furthermore, ARTON (registered trademark) series (manufactured by JSR Corporation), SURFLEN (registered trademark) series (manufactured by Mitsubishi Chemical Corporation), ZEONOR (registered trademark) series, ZEONEX (registered trademark) (each manufactured by Zeon Corporation), and the like can also be used as the olefin resin.

Acrylic Resin

The acrylic resin that can be used as a material for the substrate a is not particularly limited. Examples of the acrylic resin include homopolymers such as polymethyl methacrylate, polymethacrylic acid, polymethyl acrylate, polyacrylic acid, polyethyl methacrylate, and polyethyl acrylate and copolymers of the foregoing.

Acrylite Series, Acrypet Series, Acryplen Series (trade name, all manufactured by Mitsubishi Rayon Co., Ltd.), solvent-based acrylic resin for coating Acrydic Series (trade name, manufactured by DIC Corporation), Almatex (registered trademark, manufactured by Mitsui Chemicals, Inc.), Hitaloid (trade name, manufactured by Hitachi Chemical Company, Ltd.), and the like can also be used as the acrylic resin.

Layer b

In the laminated material according to an embodiment of the present invention, the layer b includes a crosslinked body formed of a polymer b1 including a polysiloxane structure (hereafter, also referred to as a "polymer b1") and a crosslinkable polymer b2 having at least one reactive group in Group I of reactive groups (hereafter, also referred to as a "crosslinkable polymer b2") described later. When the crosslinked body has a polysiloxane structure derived from the polymer b1, the affinity of the crosslinked body for the surface of the substrate a can be increased even if the substrate a has a low surface free energy. Thus, the layer b including the crosslinked body formed from the polymer b1 and the crosslinkable polymer b2 can be formed without causing cissing or unevenness.

Polymer b1 Including Polysiloxane Structure

The polymer b1 preferably includes, as a constituent component, at least one of an acrylic acid component, an acrylic acid ester component, an acrylamide component, or a styrene component in addition to the component having a polysiloxane structure.

The polymer b1 has a group that exhibits reactivity or interaction with the crosslinkable polymer b2 (hereafter, the group of the polymer b1 that exhibits reactivity or interaction with the crosslinkable polymer b2 is referred to as a "reactive functional group."). The polymer b1 and the crosslinkable polymer b2 react or interact with each other via such a group to form a crosslinked body. The polymer b1 preferably has, as a reactive functional group, at least one of a hydroxy group, a carboxy group, an amino group, an isocyanate group, an oxazolinyl group (oxazolyl group), an epoxy group, a vinyl group, an ethynyl group, a sulfanyl group, an azide group, a trialkoxysilyl group (preferably having 3 to 27 carbon atoms), a halogenated methyl group, or an acid anhydride structure. These reactive functional groups of the polymer b1 can interact with or react with a hydrophilic polymer to be applied onto the layer b and described later to further enhance the adhesiveness (adhesive force) between the layer b and the hydrophilic polymer. These reactive functional groups of the polymer b1 and at least one reactive group in Group I of reactive groups of the crosslinkable polymer b2 described later form a crosslinked body through a covalent bond or interaction, whereby the layer b can maintain excellent adhesiveness to the substrate a even after the passage of time as described later.

The reactive functional group of the polymer b1 is preferably at least one of a hydroxy group, a carboxy group, an amino group, an isocyanate group, an epoxy group, a trialkoxysilyl group, or a halogenated methyl group and more preferably at least one of a hydroxy group, a carboxy group, an amino group, or an isocyanate group.

The reactive functional group of the polymer b1 is preferably included in at least one of the acrylic acid component, the acrylic acid ester component, the acrylamide component, or the styrene component, which are preferred constituent components of the polymer b1.

The number of reactive functional groups in one molecule of the polymer b1 is not particularly limited as long as the effects of the present invention are not impaired. The number is normally 2 or more and is preferably 2 to 300 and more preferably 50 to 300 from the viewpoint of forming a crosslinked body with the crosslinkable polymer b2.

When the polymer b1 has a polysiloxane structure in its main chain, the average number of repetitions of polysiloxane is preferably 3 to 10000, more preferably 135 to 5000, and further preferably 200 to 1000. The average number of repetitions may be 100 or more or may be 120 or more. The content of the polysiloxane structure in the polymer b1 is preferably 1 to 70 mass %, more preferably 5 to 60 mass %, and further preferably 10 to 50 mass %.

When the polymer b1 has a polysiloxane structure in its side chain (graft chain), the average number n1 of repetitions in formula (1) below can be preferably applied. In this case, the content of the polysiloxane structure in the polymer b1 is preferably 1 to 70 mass %, more preferably 5 to 60 mass %, and further preferably 10 to 50 mass %.

The average number of repetitions can be calculated by, for example, NMR measurement.

The content of the polysiloxane structure in the polymer b1 can be calculated based on the content of Si atoms measured by NMR or the like.

The polymer b1 is preferably a graft polymer having the above-described polysiloxane structure in the graft chain from the viewpoint that the adhesiveness between the substrate a and the layer b on the substrate a can be maintained at a higher level even after the passage of time. This graft polymer preferably has a structural unit having a polysiloxane structure in the graft chain and has at least one structural unit of an acrylic acid component, an acrylic acid ester component, an acrylamide component, or a styrene component. The polymer b1 more preferably has a structural unit represented by formula (1) below and having a polysiloxane structure in the graft chain and has at least one of a structural unit represented by formula (2) below as an acrylic acid component or an acrylic acid ester component, a structural unit represented by formula (3) below as an acrylamide component, or a structural unit represented by formula (4) below as a styrene component.

Herein, the "graft polymer having a polysiloxane structure in the graft chain" refers to a polymer having a graft chain having a polysiloxane structure as a side chain bonded to a polymer main chain. That is, the graft chain is a chain that does not include atoms constituting the main chain.

Structural Unit Having Polysiloxane Structure in Graft Chain

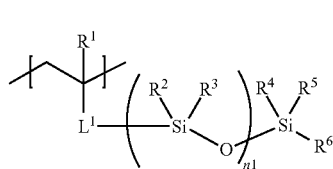

Formula (1)

In the formula (1), $R^1$ to $R^6$ represent a hydrogen atom or an organic group.

Examples of the organic group represented by $R^1$ to $R^6$ include an alkyl group, a cycloalkyl group, an alkenyl group, an aryl group, a heteroaryl group, an alkoxy group, an aryloxy group, a heteroaryloxy group, an alkylthio group, an arylthio group, a heteroarylthio group, an alkylamino group, an arylamino group, a heteroarylamino group, an alkyloxycarbonyl group, an aryloxycarbonyl group, a heteroaryloxycarbonyl group, an alkylaminocarbonyl group, an arylaminocarbonyl group, a heteroarylaminocarbonyl group, and a halogen atom. The organic group is preferably an alkyl group, a cycloalkyl group, an alkenyl group, or an aryl group.

The number of carbon atoms of the alkyl group represented by $R^1$ to $R^6$ is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

The number of carbon atoms of the cycloalkyl group represented by $R^1$ to $R^6$ is preferably 3 to 10, more preferably 5 to 10, and further preferably 5 or 6. The cycloalkyl group is preferably a three-membered ring, a five-membered ring, or a six-membered ring and more preferably a five-membered ring or a six-membered ring. Specific examples of the cycloalkyl group represented by $R^1$ to $R^6$ include cyclopropyl, cyclopentyl, and cyclohexyl.

The number of carbon atoms of the alkenyl group represented by $R^1$ to $R^6$ is preferably 2 to 10, more preferably 2 to 4, and further preferably 2. Specific examples of the alkenyl group include vinyl, allyl, and butenyl.

The number of carbon atoms of the aryl group represented by $R^1$ to $R^6$ is preferably 6 to 12, more preferably 6 to 10, and further preferably 6 to 8. Specific examples of the aryl group include phenyl, tolyl, and naphthyl.

The heteroaryl group represented by $R^1$ to $R^6$ is more preferably a five-membered or six-membered heteroaryl group having at least one of an oxygen atom, a sulfur atom, or a nitrogen atom as a ring-constituting atom. The heteroaryl group may be monocyclic or may have a fused ring. Specific examples of the heteroaryl group include 2-pyridyl, 2-thienyl, 2-furanyl, 3-pyridyl, 4-pyridyl, 2-imidazolyl, 2-benzimidazolyl, 2-thiazolyl, 2-benzothiazolyl, and 2-oxazolyl.

The preferred form of the aryl group constituting the aryloxy group, the arylthio group, the arylamino group, the aryloxycarbonyl group, and the arylaminocarbonyl group that are represented by $R^1$ to $R^6$ is the same as the form of the aryl group represented by $R^1$ to $R^6$.

The preferred form of the heteroaryl group constituting the heteroaryloxy group, the heteroarylthio group, the heteroarylamino group, the heteroaryloxycarbonyl group, and the heteroarylaminocarbonyl group that are represented by $R^1$ to $R^6$ is the same as the form of the heteroaryl group represented by $R^1$ to $R^6$.

The preferred form of the alkyl group constituting the alkoxy group, the alkylthio group, the alkylamino group, the alkyloxycarbonyl group, and the alkylaminocarbonyl group that are represented by $R^1$ to $R^6$ is the same as the form of the alkyl group represented by $R^1$ to $R^6$.

Examples of the halogen atom represented by $R^1$ to $R^6$ include a fluorine atom, a chlorine atom, a bromine atom, and an iodine atom. The halogen atom is preferably a fluorine atom or a bromine atom.

When $R^1$ to $R^6$ represent an organic group, the organic group may be unsubstituted or substituted.

$R^1$ to $R^6$ preferably represent an alkyl group, a cycloalkyl group, an alkenyl group, or an aryl group, more preferably represent an alkyl group, an alkenyl group, or an aryl group, and further preferably represent an alkyl group having 1 to 4 carbon atoms. Among them, $R^1$ to $R^5$ preferably represent a methyl group, and $R^6$ preferably represents a butyl group.

In the formula (1), $L^1$ represents a single bond or a divalent linking group.

The divalent linking group represented by $L^1$ is not particularly limited as long as the effects of the present invention are produced. When $L^1$ represents a divalent linking group, the molecular weight of $L^1$ is preferably 10 to 200, more preferably 20 to 100, and further preferably 30 to 70.

When $L^1$ represents a divalent linking group, the divalent linking group is preferably, for example, a divalent linking group obtained by combining two or more divalent groups selected from the group consisting of an alkylene group, an arylene group, —C(=O)—, —O—, and —NR$^L$—. R$^L$ represents a hydrogen atom or a substituent. When R$^L$ represents a substituent, the substituent is preferably an alkyl group. The number of carbon atoms of the alkyl group is preferably 1 to 6 and more preferably 1 to 4, and methyl or ethyl is further preferred.

The alkylene group that may constitute $L^1$ may be linear or branched. The number of carbon atoms of the alkylene group is preferably 1 to 10, more preferably 1 to 6, and further preferably 1 to 3.

The arylene group that may constitute $L^1$ preferably has 6 to 20 carbon atoms, more preferably has 6 to 15 carbon atoms, further preferably has 6 to 12 carbon atoms, and particularly preferably a phenylene group.

$L^1$ preferably represents a divalent linking group obtained by combining two or more divalent groups selected from the group consisting of an alkylene group, —C(=O)—, —O—, and —NR$^L$—.

The number of combinations of the divalent groups represented by $L^1$ is not particularly limited as long as the molecular weight of $L^1$ is satisfied, and is preferably, for example, 2 to 10.

In the formula (1), n1 represents an average number of repetitions, which is 3 to 10000. When the structural unit of the formula (1) includes a certain amount of repeating siloxane bonds, the adhesiveness between the substrate a and the layer b can be sufficiently enhanced even if the surface free energy of the surface of the substrate a on which the layer b is to be formed is low. From this viewpoint, n1 is preferably 135 to 10000, more preferably 150 to 5000, and further preferably 200 to 1000.

The average number of repetitions can be calculated by, for example, nuclear magnetic resonance (NMR) measurement.

In the polymer b1, the content of the structural unit represented by the formula (1) is preferably 1 to 70 mass %, more preferably 5 to 60 mass %, and further preferably 10 to 50 mass %.

The structural unit represented by the formula (1) can be introduced to the polymer b1 by using a macromonomer having a particular structure as a raw material. The macromonomer can be synthesized by a typical method, and a commercially available product can also be used. Examples of the commercially available product include X-22-174ASX, X-22-174BX, KF-2012, X-22-2426, and X-22-2404 (trade name, each manufactured by Shin-Etsu Chemical Co., Ltd.), AK-5, AK-30, and AK-32 (trade name, each manufactured by Toagosei Co., Ltd.), and MCR-M07, MCR-MT, MCR-M17, and MCR-M22 (trade name, each manufactured by Gelest, Inc.).

Acrylic Acid Component or Acrylic Acid Ester Component

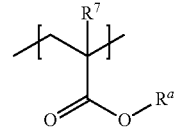

Formula (2)

In formula (2), $R^7$ and $R^a$ represent a hydrogen atom or an organic group.

The form of the organic group represented by $R^7$ may be the form of the organic group represented by $R^1$ in the above formula (1). Among them, $R^7$ preferably represents a hydrogen atom or an alkyl group. The number of carbon atoms of the alkyl group is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

The form of the organic group represented by $R^a$ may be the form of the organic group represented by $R^1$ in the above formula (1). Among them, $R^a$ preferably represents a hydrogen atom, an alkyl group, or an aryl group.

The alkyl group represented by $R^a$ preferably has 1 to 10 carbon atoms and more preferably has 1 to 6 carbon atoms. Specific examples of the alkyl group include methyl, ethyl, n-propyl, isopropyl, n-butyl, isobutyl, n-hexyl, n-octyl, 2-ethylhexyl, and n-decyl.

The aryl group represented by $R^a$ preferably has 6 to 12 carbon atoms, more preferably has 6 to 10 carbon atoms, further preferably has 6 to 8 carbon atoms, and particularly preferably has 6 carbon atoms. Specific examples of the aryl group include phenyl, tolyl, and naphthyl.

When $R^7$ and $R^a$ represent an organic group, the organic group may be unsubstituted or substituted. When the polymer b1 has the structural unit represented by the formula (2), at least a part of the structural units represented by the formula (2) in the polymer b1 preferably has the above-described reactive functional group of the polymer b1 as a substituent.

In the structural unit represented by the formula (2) that may be present in the polymer b1, when $R^a$ represents an alkyl group having a substituent, $R^a$ also preferably represents a group represented by formula (5) below in at least a part of the structural units.

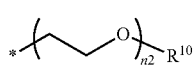

Formula (5)

In the formula (5), n2 represents an average number of repetitions, which is 1 to 10000. Herein, n2 preferably represents 1 to 8000, more preferably represents 1 to 5000, and further preferably represents 1 to 3000.

The average number of repetitions can be calculated by, for example, NMR measurement.

$R^{10}$ represents a hydrogen atom or an organic group. The form of the organic group represented by $R^{10}$ may be the form of the organic group represented by $R^1$ in the above formula (1). When $R^{10}$ represents an organic group, the organic group may be unsubstituted or substituted. $R^{10}$ preferably represents a hydrogen atom or an alkyl group. Specific examples of the alkyl group include methyl, ethyl, n-propyl, isopropyl, n-butyl, isobutyl, n-hexyl, n-octyl, 2-ethylhexyl, and n-decyl.

* represents a bonding site to an oxygen atom (—O—) in the formula (2).

$R^a$ also preferably represents a nitrogen-containing organic group in at least a part of the structural units represented by the formula (2) that may be present in the polymer b1. The molecular weight of the nitrogen-containing organic group is preferably 10 to 200 and more preferably 20 to 100. The nitrogen-containing organic group is preferably an amino group (including a substituted amino group in addition to an unsubstituted amino group). Preferred examples of the nitrogen-containing organic group include an alkylamino group, an alkylaminoalkyl group, an arylamino group, an arylaminoalkyl group, a heteroarylamino group, and a heteroarylaminoalkyl group.

When $R^a$ represents the group represented by the formula (5) or the nitrogen-containing organic group, it is believed that the interaction between the polymer b1 and the crosslinkable polymer b2 is strengthened.

Acrylamide Component

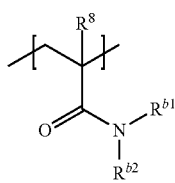

Formula (3)

In the formula (3), $R^8$, $R^{b1}$, and $R^{b2}$ represent a hydrogen atom or an organic group.

The form of the organic group represented by $R^8$ may be the form of the organic group represented by $R^1$ in the above formula (1). $R^8$ preferably represents a hydrogen atom or an alkyl group and more preferably represents an alkyl group. The number of carbon atoms of the alkyl group is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

The organic group represented by $R^{b1}$ and $R^{b2}$ is, for example, the organic group represented by $R^1$ in the above formula (1). In particular, $R^{b1}$ and $R^{b2}$ preferably represent a hydrogen atom, an alkyl group, or an aryl group. The number of carbon atoms of the aryl group is preferably 6 to 12, more preferably 6 to 10, further preferably 6 to 8, and particularly preferably 6. Specific examples of the aryl group include phenyl, tolyl, and naphthyl.

When $R^8$, $R^{b1}$, and $R^{b2}$ represent an organic group, the organic group may be unsubstituted or substituted. When the polymer b1 has the structural unit represented by the formula (3), at least a part of the structural units represented by the formula (3) in the polymer b1 preferably has the above-described reactive functional group of the polymer b1 as a substituent.

Styrene Component

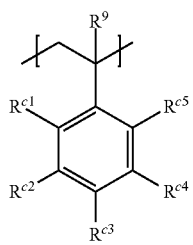

Formula (4)

In the formula (4), $R^9$ represents a hydrogen atom or an organic group. $R^{c1}$ to $R^{c5}$ represent a hydrogen atom, a halogen atom, or an organic group.

The form of the organic group represented by $R^9$ may be the form of the organic group represented by $R^1$ in the above formula (1). In particular, $R^9$ preferably represents a hydrogen atom.

The form of the organic group represented by $R^{c1}$ to $R^{c5}$ may be the form of the organic group represented by $R^1$ in the above formula (1). The halogen atom represented by $R^{c1}$ to $R^{c5}$ is not particularly limited. The halogen atom is preferably a fluorine atom or a bromine atom and more preferably a fluorine atom. $R^{c1}$ to $R^{c5}$ preferably represent a hydrogen atom, an alkyl group, or a halogen atom. The number of carbon atoms of the alkyl group is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

When $R^9$ and $R^{c1}$ to $R^{c5}$ represent an organic group, the organic group may be unsubstituted or substituted. When the polymer b1 has the structural unit represented by the formula (4), at least a part of the structural units represented by the formula (4) in the polymer b1 preferably has the above-described reactive functional group of the polymer b1 as a substituent.

When the polymer b1 has a structural unit represented by any of the formulae (2) to (4), the total amount of the structural unit in the polymer b1 is preferably 10 to 90 mass %, more preferably 15 to 80 mass %, and further preferably 20 to 70 mass %. The total amount of the structural unit may be 30 to 99 mass %, 40 to 95 mass %, or 50 to 90 mass %.

When the polymer b1 has a structural unit that is represented by any of the formulae (2) to (4) and that has the above-described reactive functional group of the polymer b1, the content of the structural unit in the polymer b1 is preferably 5 to 70 mass %, more preferably 10 to 50 mass %, further preferably 10 to 30 mass %, and particularly preferably 15 to 30 mass %. In this case, a structural unit other than the structural unit that is represented by any of the formulae (2) to (4) and that has the above-described reactive functional group of the polymer b1 is preferably used in combination.

The polymer b1 may have a structural unit other than the structural unit represented by the formula (1) and the structural unit represented by any of the formulae (2) to (4) as long as the effects of the present invention are produced.

The polymer b1 can be synthesized by a typical method. For example, the polymer b1 is obtained by reacting a monomer that results in a desired structural unit and a polymerization initiator by a typical method. The polymerization reaction may be any of anionic polymerization, cationic polymerization, and radical polymerization, but radical polymerization is preferred. The polymer obtained by the polymerization reaction is also preferably subjected to purification by a reprecipitation method or the like.

When the composition according to an embodiment of the present invention is prepared, the polymer b1 may be provided in the form of either solution or solid.

Any polymerization initiator can be used in accordance with the form of the polymerization reaction (anionic polymerization, cationic polymerization, or radical polymerization). The polymerization initiator may be either a thermal polymerization initiator or a photopolymerization initiator. The molecular weight of the polymerization initiator is not limited, and any polymerization initiator having a low molecular weight to a high molecular weight may be used.

Specific examples of the radical polymerization initiator include organic peroxides and azo compounds.

Other examples include high-molecular-weight polymerization initiators having a peroxide structure or an azo structure in the polymer chain (preferably in the main chain), such as a peroxide high-molecular-weight polymerization initiator and an azo high-molecular-weight polymerization initiator.

The high-molecular-weight polymerization initiator also preferably has the above-described polysiloxane structure. The high-molecular-weight polymerization initiator having a polysiloxane structure functions as a polymerization initiator and also serves as the above-described constituent component having a polysiloxane structure. Thus, the polymer b1 can be obtained.

The number of peroxide structures or azo structures in the high-molecular-weight polymerization initiator is not particularly limited, but is preferably 2 or more. The weight-average molecular weight of the high-molecular-weight polymerization initiator is also not particularly limited.

Any commercially available high-molecular-weight polymerization initiator can be used. The polymerization initiator is, for example, a polydimethylsiloxane unit-containing high-molecular-weight azo polymerization initiator VPS-1001N (trade name, manufactured by Wako Pure Chemical Industries, Ltd.).

The weight-average molecular weight of the polymer b1 is preferably 5000 to 300000, more preferably 10000 to 150000, and further preferably 20000 to 120000. Crosslinkable polymer b2 having at least one reactive group in Group I of reactive groups The crosslinkable polymer b2 according to an embodiment of the present invention is at least one of polysaccharides, polyethyleneimines, polyesters, polyethers, polyamides, polyurethanes, polyureas, or polyimides each having at least one reactive group in Group I of reactive groups (hereafter also referred to as a "reactive group I").

Herein, the number-average molecular weight of the crosslinkable polymer b2 is 1000 or more from the viewpoint of suppressing plasticization of the layer b and imparting mechanical strength exhibiting excellent adhesiveness even after the passage of time. The number-average molecular weight of the crosslinkable polymer b2 is preferably 1000 to 300000, more preferably 1500 to 300000, further preferably 2000 to 200000, and still further preferably 3000 to 100000. The crosslinkable polymer b2 may be an oligomer as long as the above number-average molecular weight is satisfied. Hereafter, the term "polymer" simply referred to includes oligomers in addition to polymers.

Group I of Reactive Groups hydroxy group, carboxy group, amino group, isocyanate group, oxazolinyl group, epoxy group, vinyl group, ethynyl group, sulfanyl group, azide group, trialkoxysilyl group, halogenated methyl group, and acid anhydride structure The adhesiveness between the substrate a and the layer b disposed on the substrate a can be improved by forming a bond between a material for the layer b and the substrate a or by increasing the mechanical strength of the material for the layer b. It is believed that the decrease in adhesiveness over time is mainly caused by plasticization of the layer b due to, for example, bleed-out of low-molecular-weight components in the substrate a to the interface between the substrate a and the layer b on the substrate a or adsorption of carbon dioxide in the air to the layer b. In the laminated material according to an embodiment of the present invention, it is presumed that since the crosslinkable polymer b2 constituting the crosslinked body is the above-described polymer having a negative element in the main chain, the interaction between polymer chains constituting the crosslinked body increases, which can form a stronger layer b. In the laminated material according to an embodiment of the present invention having such a layer b, it is presumed that as a result of suppression of the plasticization of the layer b, a decrease in adhesiveness over time is suppressed, and sufficiently high adhesiveness can be maintained even after the passage of time. Even when a polymer having a negative element in the main chain is used as the polymer b1, it is difficult to produce the effects of the present invention at a desired level because a coating solution for forming the layer b gelates through self-crosslinking.

The "main chain" refers to a molecular chain to which a branched chain or a side chain is bonded as a pendant when the main chain has a branched chain or a side chain from the main chain (with respect to the main chain).

The "negative element" refers to at least one of an oxygen element or a nitrogen element.

The crosslinkable polymer b2 is a polymer that has the reactive group I described above and thereby forms a crosslinked body through an interaction or a covalent bond with the polymer b1. That is, the term "crosslinked body" in the present invention is used in a broad sense so as to include a crosslinked body in which the polymer b1 and the crosslinkable polymer b2 are crosslinked through a covalent bond and a crosslinked body in which the polymer b1 and the crosslinkable polymer b2 interact with each other through an intermolecular interaction such as an electrostatic interaction and a hydrogen bond.

The crosslinked body according to an embodiment of the present invention preferably includes at least one of a crosslinked body provided through at least one of an electrostatic interaction or a hydrogen bond or a crosslinked body provided through a covalent bond from the viewpoint of initial adhesiveness, and more preferably includes a crosslinked body provided through a covalent bond from the viewpoint of maintaining excellent adhesiveness even after the passage of time.

The reaction for forming a covalent bond (crosslinking reaction) can be caused by a typical method in accordance with the type of reactive group contributing to the crosslinking reaction.

The crosslinked body according to an embodiment of the present invention may have a crosslinked structure through another interaction or covalent bond in which the reactive group I and the reactive functional group are not involved as long as the crosslinked body is formed through the interaction or covalent bond between the reactive group I of the crosslinkable polymer b2 and the reactive functional group of the polymer b1 and the desired effects of the present invention are produced.

(1) Polymer Type

The crosslinkable polymer b2 according to an embodiment of the present invention is classified into at least one polymer type of polysaccharides, polyethyleneimines, polyesters, polyethers, polyamides, polyurethanes, polyureas, or polyimides.

In this specification, the polysaccharide refers to a polymer in which 10 or more monosaccharides are condensed (for example, bonded through a glycoside bond), and is classified into a category different from that of polyether. That is, in the present invention, the term "polyether" does not include a form in which monosaccharides are condensed.

In this specification, the polyethyleneimine may be any polymer obtained by polymerizing ethyleneimine, and may be a linear amine or a branched amine including a tertiary amine. The polyethyleneimine may also be a modified polyethyleneimine obtained by modifying active hydrogen of an amino group of polyethyleneimine.

Commercially available polymers are classified into the above polymer types in accordance with the classification of manufacturers. The classification of commercially available polymers that are not classified into the above polymer types and synthesized polymers into the polymer types of the crosslinkable polymer b2 excluding polysaccharides and polyethyleneimines is dependent on bonds in the main chain of the polymer. In the case of a polymer having two or more bonds of an ester bond, an ether bond, an amide bond, a urethane bond, a urea bond, and an imide bond in the main chain, the polymer is classified on the basis of the bond having the largest number in the main chain. For example, when the number of ester bonds is the largest, the polymer is classified into polyester. The crosslinkable polymer b2 preferably does not have, in the main chain, a bond other than bonds that specify the polymer type (an ester bond in the case of polyester, a polyether bond in the case of polyether, an amide bond in the case of polyamide, a urethane bond in the case of polyurethane, a urea bond in the case of polyurea, and an imide bond in the case of polyimide).

The crosslinkable polymer b2 is preferably at least one of polysaccharides, polyethyleneimines, polyesters, polyethers, polyamides, or polyurethanes from the viewpoint of maintaining the adhesiveness between the substrate a and the layer b at a higher level even after the passage of time.

Polysaccharides

Examples of the polysaccharides include carboxymethyl cellulose, sodium carboxymethyl cellulose, pectin (e.g., derived from citrus), protein A agarose, and hyaluronic acid (e.g., derived from cockscomb).

Polyester

Examples of the polyester include a water-soluble polyester resin Plas Coat (trade name, manufactured by GOO Chemical Co., Ltd.) and an aqueous polyester resin Aron Melt PES (trade name, manufactured by Toagosei Co., Ltd.).

Polyether

Examples of the polyether include polyethylene glycol, polypropylene glycol, and polybutylene glycol.

Polyethyleneimine

Examples of the polyethyleneimine include EPOMIN (registered trademark, manufactured by Nippon Shokubai Co., Ltd.), linear polyethyleneimine, branched polyethyleneimine, and branched polyethyleneimine-graft-polyethylene glycol.

Polyamide

Examples of the polyamide include AQ nylon (trade name, manufactured by Toray Industries, Inc.), water-soluble nylon FR-700E (trade name, manufactured by Namariichi Co., Ltd.), and Torlon (registered trademark, manufactured by Solvay).

Polyurethane

Examples of the polyurethane include Coronate (registered trademark, manufactured by Tosoh Corporation), aqueous urethane resins (manufactured by NICCA CHEMICAL Co., Ltd.), DURANATE (trade name, manufactured by Asahi Kasei Corporation), and BURNOCK (trade name, manufactured by DIC Corporation).

Polyurea

Examples of the polyurea include Kemko 189 (manufactured by Cement Works).

Polyimide

Examples of the polyimide include UPIA NF-1001 (registered trademark, manufactured by Ube Industries, Ltd.).

(2) Reactive Group I

As described above, the crosslinkable polymer b2 according to an embodiment of the present invention has at least one reactive group I in Group I of reactive groups.

Group I of Reactive Groups hydroxy group, carboxy group, amino group, isocyanate group, oxazolinyl group, epoxy group, vinyl group, ethynyl group, sulfanyl group, azide group, trialkoxysilyl group, halogenated methyl group, and acid anhydride structure The crosslinked structure formed by the reactive group I of the crosslinkable polymer b2 and the polymer b1 is, for example, as follows.

(i) Hydrogen Bond (Polar Interaction)

The crosslinked structure is formed through a hydrogen bond between the reactive group I such as a hydroxy group, a carboxy group, an amino group, or a sulfanyl group of the crosslinkable polymer b2 and the reactive functional group such as a hydroxy group, a carboxy group, an amino group, or a sulfanyl group of the polymer b1.

In addition to the above hydrogen bond, a hydrogen bond formed between a bond (e.g., an amide bond, a urethane bond, and an ester bond) of the crosslinkable polymer b2 and a reactive functional group such as a hydroxy group of the polymer b1 is also exemplified as a hydrogen bond contributing to formation of the crosslinked structure.

(ii) Covalent Bond

Examples of the covalent bond include covalent bonds formed through a reaction between the reactive group I such as a hydroxy group, a carboxy group, an amino group, an isocyanato group, an oxazolinyl group, an epoxy group, a vinyl group, an ethynyl group, a sulfanyl group, an azide group, a trialkoxysilyl group, or a halogenated methyl group of the crosslinkable polymer b2 and the reactive functional group such as a hydroxy group, a carboxy group, an amino group, an isocyanato group, an oxazolinyl group, an epoxy group, a vinyl group, an ethynyl group, a sulfanyl group, an azide group, a trialkoxysilyl group, or a halogenated methyl group of the polymer b1; and covalent bonds formed through a reaction between the reactive group I of the crosslinkable polymer b2 and a bond of the polymer b1, such as an ester bond or an amide bond.

The covalent bond can be appropriately formed in accordance with the reactive group I, the reactive functional group, and the type of bond that contribute to the reaction. Specific examples of such a covalent bond include an ester bond, an ether bond, a thioether bond, an amide bond, a urethane bond, a urea bond, an imide bond, and a C—C bond. When one of the reactive group I and the reactive functional group is a group having a ring structure, a covalent bond including two types of the above bonds can be formed through ring-opening of the ring structure. The covalent bond is, for example, a covalent bond including an amide bond and an ester bond (also simply referred to as an amide-ester bond) and formed through a reaction between an oxazolinyl group and a carboxy group.

Group I of reactive groups preferably includes a hydroxy group, a carboxy group, an amino group, an isocyanate group, an epoxy group, a trialkoxysilyl group, and a halogenated methyl group and more preferably includes a hydroxy group, a carboxy group, an amino group, an epoxy group, a trialkoxysilyl group, and a halogenated methyl group from the viewpoint of maintaining the adhesiveness between the substrate a and the layer b at a higher level even after the passage of time.

This is because these functional groups have higher reactivity and are more likely to form the crosslinked structure.

The number of reactive groups I in one molecule of the crosslinkable polymer b2 is not particularly limited as long as the effects of the present invention are not impaired. The number is normally 2 or more and is preferably 2 to 300 and more preferably 50 to 300 from the viewpoint of forming a crosslinked body with the crosslinkable polymer b1.

The content of constituent components derived from the polymer b1 in the crosslinked body is preferably 5 mass % or more, more preferably 10 mass % or more, and further preferably 20 mass % or more. The content of the polymer b1 in the crosslinked body is also preferably 40 mass % or more, more preferably 60 mass % or more, and further preferably 80 mass % or more. In the crosslinked body, the content of constituent components derived from the crosslinkable polymer b2 (that is, the content of constituent components derived from the crosslinkable polymer b2 relative to the total amount of constituent components derived from the polymer b1 and constituent components derived from the crosslinkable polymer b2) is preferably 15 to 90 mass %, more preferably 20 to 90 mass %, still more preferably 30 to 90 mass %, and further preferably 40 to 80 mass %.

The content of constituent components derived from the polymer b1 and the crosslinkable polymer b2 in the crosslinked body can also be read as the content of the polymer b1 (including the constituent components derived from the polymer b1) and the crosslinkable polymer b2 (including the constituent components derived from the crosslinkable polymer b2) in the layer b. That is, the layer b may include at least one of a polymer b1 or a crosslinkable polymer b2 that does not contribute to formation of the crosslinked body as long as the effects of the present invention are not impaired.

The polymers b1 and the crosslinkable polymers b2 constituting the crosslinked body may be each independently used alone or in combination of two or more.

The crosslinked body may include components other than the polymer b1 and the crosslinkable polymer b2 as long as the effects of the present invention are not impaired. Also in this case, the content of the polymer b1 and the crosslinkable polymer b2 in the crosslinked body is as described above.

When the layer b includes a component other than the crosslinked body, examples of the component other than the crosslinked body include a polymer binder, a surfactant, polymer fine particles, and inorganic fine particles.

The surface of the layer b is preferably subjected to hydrophilic treatment. The hydrophilic treatment of the layer b improves the adhesiveness between a layer c described later and the layer b and also increases the rate of reaction at a reaction site between the polymer b1 and the crosslinkable polymer b2. Thus, the adhesiveness between the substrate a and the layer b can be probably maintained at a higher level even after the passage of time. In the present invention, the "surface of the layer b" means a surface opposite to a surface of the layer b in contact with the substrate a.

The method of hydrophilic treatment is not particularly limited as long as a hydrophilic group can be provided to the surface of the layer b (a crosslinked body that is present on the surface of the layer b and is formed from the polymer b and the crosslinkable polymer b2). For example, the surface of the layer b can be hydrophilized by immersion in an acidic solution, immersion in an alkaline solution, immersion in a peroxide solution, plasma treatment, or electron beam irradiation.

The thickness of the layer b is normally 0.01 to 100 μm, preferably 0.05 to 50 μm, and more preferably 0.1 to 10 μm.

Method for Producing Laminated Material According to Embodiment of the Present Invention The laminated material according to an embodiment of the present invention is a laminated material used for a medical lubricating member and having a substrate a and a layer b disposed on the substrate a. The layer b can be formed by applying, onto the substrate a, a composition (the composition according to an embodiment of the present invention) including the polymer b1 and the crosslinkable polymer b2 and forming a layer including a crosslinked body formed of the polymer b1 and the crosslinkable polymer b2.

The method of applying the composition is not particularly limited. Examples of the method include a method in which the substrate a is immersed in the composition, a method in which the composition is applied onto the substrate a with a roll, and a method in which the composition is applied onto the substrate a with a cast.

The method for producing a laminated material according to an embodiment of the present invention may include a heating step. The heating conditions are, for example, 40° C. to 170° C. and 10 to 120 minutes.

The method for forming a layer including the crosslinked body and the stage at which the crosslinked body is formed are not particularly limited. The layer may be formed by any typical method as long as the crosslinked body is formed at the stage at which the laminated material according to an embodiment of the present invention has been produced and the produced laminated material exhibits the desired effects of the present invention.

When the crosslinked body is a crosslinked body formed through a covalent bond, a reaction of forming the crosslinked body is preferably caused by heating or irradiation with light. This heating is preferably performed by the heating step described above. The heating conditions in this case are preferably appropriately adjusted in accordance with the chemical reaction between the polymer b1 and the crosslinkable polymer b2 that forms covalent bonds serving as crosslinking points. For the irradiation with light, the crosslinked body is preferably formed by, for example, irradiation with ultraviolet light (300 to 400 nm, 30 mW/cm$^2$) for 3 minutes.

The method for producing a laminated material according to an embodiment of the present invention may include a hydrophilic treatment. The method described in the hydrophilic treatment of the surface of the layer b is used as the hydrophilic treatment method.

Medical Lubricating Member

Figure 2:
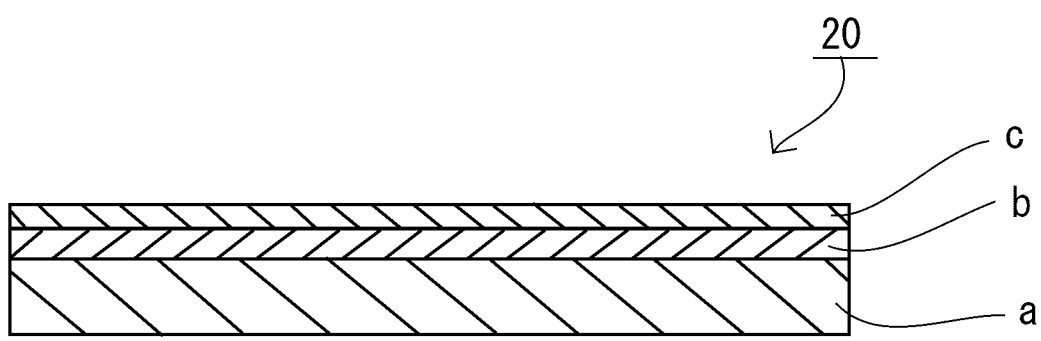
FIG. 2 is a longitudinal sectional view illustrating a medical lubricating member according to an embodiment of the present invention.

The medical lubricating member according to an embodiment of the present invention is provided by forming a layer c including a hydrophilic polymer (also referred to as a "hydrophilic lubricating coating layer" or a "layer c") on the surface of the layer b constituting the laminated material according to an embodiment of the present invention. That is, as illustrated in FIG. 2 (FIG. 2 illustrates one embodiment in which a medical lubricating member is produced using the laminated material in FIG. 1), the medical lubricating member according to an embodiment of the present invention has the laminated material according to an embodiment of the present invention and a layer c including a hydrophilic polymer and disposed on the layer b (the surface of the layer b) constituting the laminated material. Examples of the hydrophilic polymer include polyvinylpyrrolidone, a vinyl ether-maleic anhydride copolymer, polyethylene glycol, polyacrylic acid, polyacrylamide, and hyaluronic acid. One or more of the hydrophilic polymers can be used. The hydrophilic polymer is preferably at least one of polyvinylpyrrolidone, a vinyl ether-maleic anhydride copolymer, or polyethylene glycol.

The content of the hydrophilic polymer in the layer c is preferably 50 mass % or more, more preferably 70 mass % or more, further preferably 80 mass % or more, and particularly preferably 90 mass % or more. When the layer c includes a component other than the hydrophilic polymer, examples of the component other than the hydrophilic polymer include a polymer binder, a surfactant, polymer fine particles, inorganic fine particles, and a crosslinking agent.

The layer c can be formed by preparing a solution (a coating solution for forming a layer c) in which the above-described hydrophilic polymer is dissolved, applying this solution onto the layer b, and drying the solution. The solution may contain a crosslinking agent in accordance with the purpose. Examples of the solvent used for the coating solution for forming a layer c include ether solvents such as dibutyl ether, dimethoxymethane, dimethoxyethane, diethoxyethane, propylene oxide, 1,4-dioxane, 1,3-dioxolane, 1,3,5-trioxane, tetrahydrofuran, anisole, and phenetole; ketone solvents such as acetone, methyl ethyl ketone, diethyl ketone, dipropyl ketone, diisobutyl ketone, methyl isobutyl ketone, cyclopentanone, cyclohexanone, methylcyclohexanone, and dimethylcyclohexanone; ester solvents such as ethyl formate, propyl formate, n-pentyl formate, methyl acetate, ethyl acetate, methyl propionate, ethyl propionate, n-pentyl acetate, and γ-butyrolactone; alcohol solvents such as methanol, ethanol, 1-propanol, 2-propanol, 1-butanol, 2-butanol, tert-butanol, 1-pentanol, 2-methyl-2-butanol, and cyclohexanol; aromatic hydrocarbon solvents such as xylene and toluene; halogenated hydrocarbon solvents such as methylene chloride, chloroform, and 1,1-dichloroethane; amide solvents such as N-methyl-2-pyrrolidone (NMP), N,N-dimethylformamide (DMF), and N,N-dimethylacetamide (DMAc); nitrile solvents such as acetonitrile; and organic solvents having two or more functional groups, such as methyl 2-methoxyacetate, methyl 2-ethoxyacetate, ethyl 2-ethoxyacetate, ethyl 2-ethoxypropionate, 2-methoxyethanol, 2-propoxyethanol, 2-butoxyethanol, 1,2-diacetoxyacetone, acetylacetone, diacetone alcohol, methyl acetoacetate, propylene glycol monomethyl ether acetate, and ethyl acetoacetate.

Examples of the crosslinking agent included in the coating solution for forming a layer c include a polyisocyanate compound (preferably a diisocyanate compound), a silane coupling agent, a titanium coupling agent, a polyepoxy compound, a polyamine compound, and a melamine compound.

The thickness of the layer c is preferably 0.1 to 100 m, more preferably 0.5 to 50 m, and further preferably 1 to 10 m.

The medical lubricating member according to an embodiment of the present invention is preferably used as a member of a medical device. The medical lubricating member according to an embodiment of the present invention is normally used such that the layer c serves as an outermost surface of the medical device (at least one of an inner surface of a tube or an outer surface of a tube).

In the present invention, the medical device is not particularly limited. Examples of the medical device include a medical tube, a guide wire, an endoscope, a surgical needle, a surgical suture, forceps, an artificial blood vessel, an artificial heart, and a contact lens. In particular, the medical device to which the medical lubricating member according to an embodiment of the present invention is applied is preferably an endoscope, a guide wire, a medical tube, or a surgical needle.

Medical Device

The medical device according to an embodiment of the present invention is formed using the medical lubricating member according to an embodiment of the present invention. The medical device is not particularly limited and is at least one of a medical tube, a guide wire, an endoscope, a surgical needle, a surgical suture, forceps, an artificial blood vessel, an artificial heart, or a contact lens. In particular, the medical device according to an embodiment of the present invention is preferably an endoscope, a guide wire, a medical tube, or a surgical needle.

EXAMPLES

Hereafter, the present invention will be further described in detail based on Examples. The present invention should not be construed as being limited to Examples.

In the chemical structures of the following polymers 1 and 2, the structure enclosed by [ ] indicates a structural unit, and the structure enclosed by ( ) indicates a repeating structure.

1. Preparation of Polymer and Polymer Solution

Synthesis Example (Synthesis of Polymer 1)

Seventy grams of a polydimethylsiloxane unit-containing high-molecular-weight azo polymerization initiator VPS-1001N (trade name, manufactured by Wako Pure Chemical Industries, Ltd., weight-average molecular weight of polysiloxane unit: 10000) and 30 g of 2-hydroxyethyl methacrylate were mixed and stirred at 75° C. for 4 hours in a nitrogen atmosphere to cause a polymerization reaction. The resulting reaction solution was added to 1000 mL of methanol to generate a white solid. The resulting white solid was washed with methanol and dried to obtain a polymer 1. The weight-average molecular weight of the polymer 1 was 35000. In the following structural formula of the polymer 1, the average number of repeating units of poly dimethylsiloxane is 130.

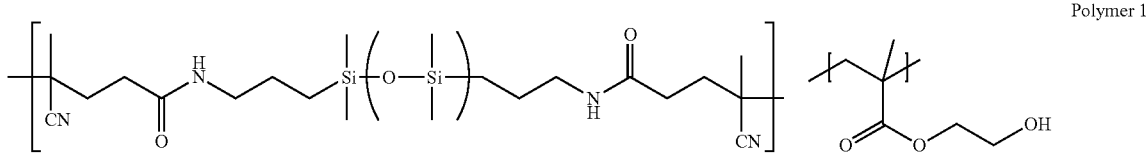

Polymer 1

Synthesis Example (Synthesis of Solution of Polymer 2)

To a reaction apparatus equipped with a reflux column and a stirrer, 16.0 g of silicone macromer AK-32 (trade name, manufactured by Toagosei Co., Ltd., number-average molecular weight: 20000), 4.0 g of hydroxyethyl methacrylate (manufactured by Tokyo Chemical Industry Co., Ltd.), 10.0 g of methoxy polyethylene glycol methacrylate (hereafter referred to as MPEGA) (manufactured by Aldrich, number-average molecular weight: 5000), 10.0 g of methyl methacrylate (manufactured by Tokyo Chemical Industry Co., Ltd.), 0.03 g of azobisisobutyronitrile (AIBN) (manufactured by Wako Pure Chemical Industries, Ltd.), and 60 g of methyl ethyl ketone (MEK) (manufactured by Wako Pure Chemical Industries, Ltd.) were added, and stirring was performed at 80° C. for 20 hours to cause a polymerization reaction. The obtained reaction solution was used as a solution of the polymer 2. The weight-average molecular weight of the polymer 2 was 20000. In the structural formula of the polymer 2, the average number of repeating units of polydimethylsiloxane is 267.

Polymer 2

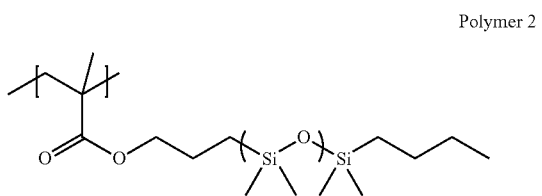

-continued

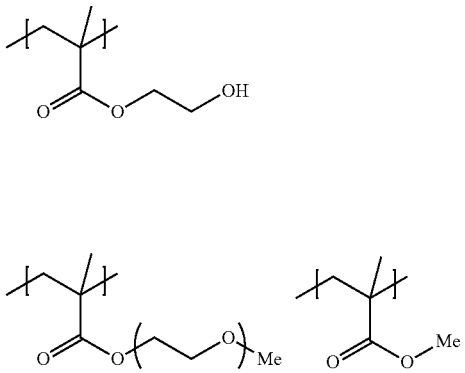

Synthesis Example (Synthesis of Polymer 3)

Seventy grams of a polydimethylsiloxane unit-containing high-molecular-weight azo polymerization initiator VPS-1001N (trade name, manufactured by Wako Pure Chemical Industries, Ltd., weight-average molecular weight of polysiloxane unit: 10000) and 30 g of 2-isopropenyl-2-oxazoline were mixed and stirred at 75° C. for 4 hours in a nitrogen atmosphere to cause a polymerization reaction. The resulting reaction solution was added to 1000 mL of methanol to generate a white solid. The resulting white solid was washed with methanol and dried to obtain a polymer 3. The weight-average molecular weight of the polymer 3 was 35000. In the following structural formula of the polymer 3, the average number of repeating units of poly dimethylsiloxane is 130.

Polymer 3

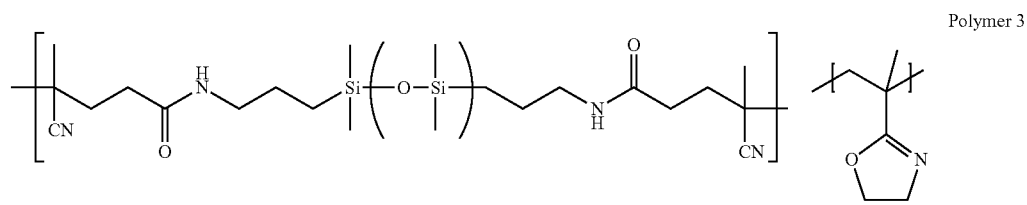

2. Preparation of Coating Solution for Forming Layer b

A polymer or a polymer solution, a crosslinkable polymer, and optionally a photopolymerization initiator were dissolved in a solvent in amounts shown in Table 1 below to prepare coating solutions 1 to 18 for forming a layer b. In Table 1, the amount is expressed in units of parts by mass, and "-" means that the corresponding component is not contained.

TABLE 1

|  |  | Coating solution for forming layer b | | | | | | | | |
|---|---|---|---|---|---|---|---|---|---|---|
|  |  | 1 | 2 | 3 | 4 | 5 | 6 | 7 | 8 | 9 |
| Polymer b1 | Polymer 1 | 2.0 | — | 2.0 | — | 2.0 | 2.0 | 2.0 | 2.0 | 2.0 |
|  | Polymer 2 (solution) | — | 5.0 | — | — | — | — | — | — | — |
|  | Polymer 3 | — | — | — | 2.0 | — | — | — | — | — |
|  | Polymer in Example 1 of JP2008-289864A | — | — | — | — | — | — | — | — | — |
| Crosslinkable polymer b2 | UPIA NF-1001 | 0.5 | 0.5 | — | 0.5 | — | — | — | — | — |
|  | EPOMIN | — | — | — | 0.5 | — | — | — | — | — |
|  | CMC | — | — | — | — | 0.5 | — | — | 2.0 | 8.0 |
|  | FR-700E | — | — | — | — | — | 0.5 | — | — | — |
|  | Coronate (solution) | — | — | — | — | — | — | 0.9 | — | — |
|  | TEGDM | — | — | — | — | — | — | — | — | — |
|  | Polybutadiene | — | — | — | — | — | — | — | — | — |
| Photopolymerization initiator | IRGACURE 819 | — | — | — | — | — | — | — | — | — |
| Solvent | Isopropyl alcohol | 97.5 | 94.5 | 97.5 | 97.5 | 97.5 | 97.5 | 97.1 | 96 | 90 |
|  | Total | 100 | 100 | 100 | 100 | 100 | 100 | 100 | 100 | 100 |

|  |  | Coating solution for forming layer b | | | | | | | | |
|---|---|---|---|---|---|---|---|---|---|---|
|  |  | 10 | 11 | 12 | 13 | 14 | 15 | 16 | 17 | 18 |
| Polymer b1 | Polymer 1 | 2.0 | 2.0 | — | — | — | — | — | — | — |
|  | Polymer 2 (solution) | — | — | — | 5.0 | 5.0 | 5.0 | 5.0 | 5.0 | 5.0 |
|  | Polymer 3 | — | — | — | — | — | — | — | — | — |
|  | Polymer in Example 1 of JP2008-289864A | — | — | 2.0 | — | — | — | — | — | — |
| Crosslinkable polymer b2 | UPIA NF-1001 | — | — | — | — | — | — | — | — | — |
|  | EPOMIN | — | — | — | — | 0.5 | — | — | — | — |
|  | CMC | — | — | — | — | — | 0.5 | — | 2.0 | 8.0 |
|  | FR-700E | — | — | — | — | — | — | 0.5 | — | — |
|  | Coronate (solution) | — | — | — | — | — | — | — | — | — |
|  | TEGDM | 0.49 | — | — | — | — | — | — | — | — |
|  | Polybutadiene | — | 0.5 | — | — | — | — | — | — | — |

TABLE 1-continued

| Photopolymerization initiator | IRGACURE 819 | 0.01 | — | — | — | — | — | — | — | — |
| Solvent | Isopropyl alcohol | 97.5 | 97.5 | 98.0 | 94.5 | 94.5 | 94.5 | 94.1 | 93.0 | 87.0 |
| | Total | 100 | 100 | 100 | 100 | 100 | 100 | 100 | 100 | 100 |

Note in Table
Polymer 2: The solution of the polymer 2 (solid content: 40 mass %) prepared above was used, and the amount of the polymer 2 in the form of solution is shown.
Polymer in Example 1 of JP2008-289864A: The polymer was prepared based on the synthesis method of a copolymer 1 in Example 1 of JP2008-289864A.
Coronate: The amount in the form of coronate solution is shown.
Details of crosslinkable polymer b2 and Presumed formation mechanism of crosslinked body
(1) Polyimide
UPIA NF-1001: UPIA NF-1001 (registered trademark), number-average molecular weight 10000, manufactured by Ube Industries, Ltd.
A crosslinked body is formed through formation of an ester bond between a carboxy group in polyamic acid remaining in UPIA and a hydroxy group in the polymer 1 or 2. Alternatively, a crosslinked body is formed through a hydrogen bond between a carboxy group in UPIA and a hydroxy group in the polymer 1 or 2.
Alternatively, a crosslinked body is formed through formation of an amide-ester bond between a carboxy group in polyamic acid remaining in UPIA and an oxazolinyl group in the polymer 3.
(2) Polyethyleneimine
EPOMIN: EPOMIN (registered trademark) SP-200, number-average molecular weight 10000, manufactured by Nippon Shokubai Co., Ltd.
A crosslinked body is formed through an amide bond formed by nucleophilic attack of an amino group in EPOMIN to an ester bond in the polymer 1 or through a hydrogen bond between an amino group in EPOMIN and a hydroxy group in the polymer 1.
(3) Polysaccharides
CMC: CMC DAICEL 1330 (trade name), sodium carboxymethyl cellulose, 1% viscosity at 25° C. at 60 rpm 50 to 100 mPa · s, degree of etherification (degree of substitution) 1.0 to 1.5, number-average molecular weight 120000, manufactured by Daicel FineChem Co., Ltd.
A crosslinked body is formed through an ester bond formed by nucleophilic attack of a hydroxy group in CMC to an ester bond in the polymer 1 or through a hydrogen bond between a carboxy group or a hydroxy group in CMC and a hydroxy group in the polymer 1.
(4) Polyamide
FR-700E: FINELEX (registered trademark) FR-700E, carboxy group-containing water-soluble nylon obtained by modifying methoxymethylated nylon, number-average molecular weight: 10000, manufactured by Namariichi Co., Ltd.
A crosslinked body is formed through formation of an ester bond between a side-chain carboxy group in FR-700E and a hydroxy group in the polymer 1. Alternatively, a crosslinked body is formed through a hydrogen bond between a side-chain carboxy group or an amide bond in the main chain in FR-700E and a hydroxy group in the polymer 1.
(5) Polyurethane
Coronate: Coronate L-55E (trade name), number-average molecular weight 2000, (manufactured by Tosoh Corporation, solid content: 55 mass %)
A crosslinked body is formed through a urethane bond formed by an addition reaction of an isocyanate group in Coronate and a hydroxy group in the polymer 1 or through a hydrogen bond between a urethane bond in Coronate and a hydroxy group in the polymer 1.
(6) Other crosslinking agents
TEGDM: tetraethylene glycol dimethacrylate, a crosslinking agent used in WO15/198919A
Polybutadiene: liquid polybutadiene NISSO-PB B-1000 (trade name), 1,2-polybutadiene homopolymer, the content of 1,2-vinyl structure 85% or more, manufactured by Nippon Soda Co., Ltd.
A crosslinked body is formed through a new C—C bond formed between a vinyl group in polybutadiene and a C—C bond in the polymer 1.
Photopolymerization initiator
IRGACURE 819: IRGACURE (registered trademark) 819, manufactured by BASF Japan 3. Production of Laminated Material-Coated Sheet Example 1

A urethane sheet having a thickness of 500 m, a width of 50 mm, and a length of 50 mm (trade name: 07-007-01, surface free energy: 38 mN/m, manufactured by Hagitec inc.) was immersed in the coating solution 1 for forming a layer b for 3 minutes and then dried by heating at 150° C. for 30 minutes to form a layer b. Thus, a laminated material-coated sheet in Example 1 was produced.

Examples 2 to 9 and 13 to 18 and Comparative Examples 1 and 2

Laminated material-coated sheets in Examples 2 to 9 and 13 to 18 and Comparative Examples 1 and 2 were produced in the same manner as in Example 1, except that coating solutions 2 to 11 for forming a layer b were used instead of the coating solution 1 for forming a layer b.
In Comparative Example 1, the layer b was formed by performing irradiation with light for 1 minute under the conditions of 365 nm and 80 mW/cm$^2$ in addition to the drying by heating.

Comparative Example 3

A laminated material-coated sheet in Comparative Example 3 was produced in the same manner as in Example 1, except that the coating solution 12 for forming a layer b was used instead of the coating solution 1 for forming a layer b and the crosslinkable polymer b2 was not used.

Example 10

A laminated material-coated sheet in Example 10 was produced in the same manner as in Example 1, except that a silicone sheet (trade name: KE-880-U, hardness 80A, manufactured by Shin-Etsu Chemical Co., Ltd., surface free energy: 22 mN/m) was used instead of the urethane sheet in Example 1.

Examples 21 to 23

Laminated material-coated sheets in Examples 21 to 23 were produced in the same manner as in Examples 14, 17, and 18, respectively, except that a silicone sheet (trade name: KE-880-U, hardness 80A, manufactured by Shin-Etsu Chemical Co., Ltd., surface free energy: 22 mN/m) was used instead of the urethane sheet in Examples 14, 17, and 18.
The thickness of the layer b in each of the sheets in Examples 1 to 10, 13 to 18, and 21 to 23 and Comparative Examples 1 to 3 was 0.7 m.

Example 11

The laminated material-coated sheet produced in Example 8 was immersed in a 10% aqueous hydrochloric acid solution for 12 hours or longer and then washed with methanol. Subsequently, the sheet was air-dried at room temperature (25° C.) for 1 hour and then dried at 60° C. for 30 minutes to produce a laminated material-coated sheet in Example 11 in which the surface of the layer b was subjected to hydrophilic treatment.

Example 19

The laminated material-coated sheet produced in Example 14 was immersed in a 10% aqueous hydrochloric acid solution for 12 hours or longer and then washed with methanol. Subsequently, the sheet was air-dried at room temperature (25° C.) for 1 hour and then dried at 60° C. for 30 minutes to produce a laminated material-coated sheet in Example 19 in which the surface of the layer b was subjected to hydrophilic treatment.

Example 24

A laminated material-coated sheet in Example 24 was produced in the same manner as in Example 19, except that a silicone sheet (trade name: KE-880-U, hardness 80A, manufactured by Shin-Etsu Chemical Co., Ltd., surface free energy: 22 mN/m) was used instead of the urethane sheet in Example 19.

Example 12

A hydrophilic coating solution was prepared by dissolving 2.0 g of polyvinylpyrrolidone (K-90 (trade name), manufactured by Wako Pure Chemical Industries, Ltd.) and 0.25 g of 4,4-diphenylmethane diisocyanate (MDI) (manufactured by Tokyo Chemical Industry Co., Ltd.) in 100 g of chloroform.

The laminated material-coated sheet produced in Example 8 was immersed in a 10% aqueous hydrochloric acid solution for 12 hours or longer, then washed with methanol, and air-dried at room temperature (25° C.) for 1 hour and then dried at 60° C. for 30 minutes. The air-dried sheet was immersed in the hydrophilic coating solution for 3 minutes, and subsequently dried by heating at 60° C. for 30 minutes and then at 135° C. for 30 minutes to form a hydrophilic lubricating coating layer c, thereby producing a laminated material-coated sheet with a hydrophilic lubricating coating layer in Example 12.

Example 20

The laminated material-coated sheet produced in Example 14 was immersed in a 10% aqueous hydrochloric acid solution for 12 hours or longer, then washed with methanol, and air-dried at room temperature (25° C.) for 1 hour and then dried at 60° C. for 30 minutes. The air-dried sheet was immersed in the hydrophilic coating solution for 3 minutes, and subsequently dried by heating at 60° C. for 30 minutes and then at 135° C. for 30 minutes to form a hydrophilic lubricating coating layer c, thereby producing a laminated material-coated sheet with a hydrophilic lubricating coating layer in Example 20.

Example 25

A laminated material-coated sheet in Example 25 was produced in the same manner as in Example 20, except that a silicone sheet (trade name: KE-880-U, hardness 80A, manufactured by Shin-Etsu Chemical Co., Ltd., surface free energy: 22 mN/m) was used instead of the urethane sheet in Example 20.

The thickness of the layer b in each of the sheets in Examples 11, 19, and 24 was 0.7 μm, and the total thickness of the layer b and the layer c in each of the sheets in Examples 12, 20, and 25 was 4.0 μm.

Test

The laminated material-coated sheets produced above were subjected to the following tests. Table 2 collectively shows the test results.

[Test Example 1-1] Initial Adhesiveness

The laminated material-coated sheets obtained above were evaluated by a tape peel test (conforming to ISO 2409).

Using a cross-cutter, the surface of the laminated material (the surface far from the substrate a) was cut in a grid pattern having a total of 100 squares (10 squares in length×10 squares in width) at 2 mm intervals. Subsequently, a cellophane tape (registered trademark, manufactured by Nichiban Co., Ltd., width 24 mm) was attached to a portion that was cut in the grid pattern, and the cellophane tape was peeled off. In each of the laminated material-coated sheets, a cut was made so as to reach the substrate a.

The percentage ([number of remaining squares/100]×100 (%)) of the number of squares at which the laminated material was left on the laminated material-coated sheet to the total number of squares was calculated. The "initial adhesiveness" was evaluated based on the following evaluation criteria. In this test, "3" or higher is acceptable.

[Test Example 1-2] Adhesiveness Overtime

The laminated material-coated sheets obtained above were stored for 2 weeks under the conditions of 40° C., 80% RH, and atmospheric pressure (1013 hPa). The laminated material-coated sheets after the passage of time were subjected to the tape peel test in the same manner as in Test example 1-1. The "adhesiveness over time" was evaluated based on the following evaluation criteria. In this test, "3" or higher is acceptable.

Evaluation Criteria of Adhesiveness

9: The percentage of remaining squares is 99% or more.

8: The percentage of remaining squares is 97% or more and less than 99%.

7: The percentage of remaining squares is 95% or more and less than 97%.

6: The percentage of remaining squares is 90% or more and less than 95%.

5: The percentage of remaining squares is 80% or more and less than 90%.

4: The percentage of remaining squares is 60% or more and less than 80%.

3: The percentage of remaining squares is 40% or more and less than 60%.

2: The percentage of remaining squares is 20% or more and less than 40%.

1: The percentage of remaining squares is less than 20%.

TABLE 2

| | Substrate a | Coating solution | Polymer b1 | Crosslinkable polymer b2 | Content of crosslinkable polymer b2 in crosslinked body [mass %]*1 | Hydrophilic treatment | Layer c | Initial adhesiveness | Adhesiveness over time |
|---|---|---|---|---|---|---|---|---|---|
| | | | | Layer b | | | | Evaluation | |
| Example 1 | Urethane | 1 | Polymer 1 | UPIA NF-1001 | 20 | No | — | 7 | 4 |
| Example 2 | Urethane | 2 | Polymer 2 | UPIA NF-1001 | 20 | No | — | 9 | 5 |
| Example 3 | Urethane | 3 | Polymer 1 | EPOMIN | 20 | No | — | 7 | 5 |
| Example 4 | Urethane | 4 | Polymer 3 | UPIA NF-1001 | 20 | No | — | 7 | 3 |
| Example 5 | Urethane | 5 | Polymer 1 | CMC | 20 | No | — | 7 | 5 |
| Example 6 | Urethane | 6 | Polymer 1 | FR-700E | 20 | No | — | 7 | 5 |
| Example 7 | Urethane | 7 | Polymer 1 | Coronate | 20 | No | — | 7 | 5 |
| Example 8 | Urethane | 8 | Polymer 1 | CMC | 50 | No | — | 7 | 6 |
| Example 9 | Urethane | 9 | Polymer 1 | CMC | 80 | No | — | 7 | 6 |
| Example 10 | Silicone | 8 | Polymer 1 | CMC | 50 | No | — | 7 | 7 |
| Example 11 | Urethane | 8 | Polymer 1 | CMC | 50 | Yes | — | 8 | 7 |
| Example 12 | Urethane | 8 | Polymer 1 | CMC | 50 | Yes | Formed | 9 | 7 |
| Example 13 | Urethane | 13 | Polymer 2 | EPOMIN | 20 | No | — | 9 | 5 |
| Example 14 | Urethane | 14 | Polymer 2 | CMC | 20 | No | — | 9 | 6 |
| Example 15 | Urethane | 15 | Polymer 2 | FR-700E | 20 | No | — | 9 | 5 |
| Example 16 | Urethane | 16 | Polymer 2 | Coronate | 20 | No | — | 9 | 5 |
| Example 17 | Urethane | 17 | Polymer 2 | CMC | 50 | No | — | 9 | 6 |
| Example 18 | Urethane | 18 | Polymer 2 | CMC | 80 | No | — | 9 | 6 |
| Example 19 | Urethane | 14 | Polymer 2 | CMC | 20 | Yes | — | 9 | 7 |
| Example 20 | Urethane | 14 | Polymer 2 | CMC | 20 | Yes | Formed | 9 | 8 |
| Example 21 | Silicone | 14 | Polymer 2 | CMC | 20 | No | — | 9 | 7 |
| Example 22 | Silicone | 17 | Polymer 2 | CMC | 50 | No | — | 9 | 7 |
| Example 23 | Silicone | 18 | Polymer 2 | CMC | 80 | No | — | 9 | 7 |
| Example 24 | Silicone | 14 | Polymer 2 | CMC | 20 | Yes | — | 9 | 8 |
| Example 25 | Silicone | 14 | Polymer 2 | CMC | 20 | Yes | Formed | 9 | 9 |
| Comparative Example 1 | Urethane | 10 | Polymer 1 | TEGDM | 20 | No | — | 7 | 1 |
| Comparative Example 2 | Urethane | 11 | Polymer 1 | Polybutadiene | 20 | No | — | 7 | 1 |
| Comparative Example 3 | Urethane | 12 | Polymer in Example 1 of JP2008-289864A | —*3 | —*2 | No | — | 2 | 1 |

Note in Table
*1 calculated from mass of crosslinkable polymer b2/(mass of polymer b1 + mass of crosslinkable polymer b2) × 100%
*2 indicating "cannot be calculated"
*3 indicating "not including the crosslinkable polymer b2"

As shown in Table 2, in Comparative Example 1, the coating solution for forming a layer b includes a tetraethylene glycol dimethacrylate having a number-average molecular weight of less than 1000 as the crosslinkable polymer. The laminated material-coated sheet in Comparative Example 1 formed by using this coating solution was inferior in terms of the evaluation result of adhesiveness over time, and excellent adhesiveness could not be maintained. In Comparative Example 2, the coating solution for forming a layer b includes, as the crosslinkable polymer, polybutadiene having no negative element in the main chain. The laminated material-coated sheet in Comparative Example 2 formed by using this coating solution had low adhesiveness over time, and excellent adhesiveness could not be maintained after the passage of time. In Comparative Example 3 having no crosslinkable polymer, the initial adhesiveness was poor. Furthermore, in Comparative Example 3, the adhesiveness further decreased after the passage of time.

In contrast, in each of Examples 1 to 12 that satisfy the requirements of the present invention, the adhesiveness over time was high, and excellent adhesiveness could be maintained even after the passage of time.

While the present invention has been described with reference to the embodiments thereof, we do not intend to limit our invention in any detail of the description unless otherwise specified. Rather, the invention should be broadly construed without departing from the spirit and scope of the invention as defined by the appended claims.

10 laminated material used for medical lubricating member
20 medical lubricating member
a substrate
b layer including crosslinked body formed of polymer b1 including polysiloxane structure and crosslinkable polymer b2.
c layer including hydrophilic polymer

What is claimed is:

1. A composition for a laminated material used for a medical lubricating member, the composition comprising:
   a polymer b1 including a polysiloxane structure; and
   a crosslinkable polymer b2 having a reactive group that forms a crosslinked body with the polymer b1,
   wherein the reactive group is at least one reactive group in Group I of reactive groups,
   the crosslinkable polymer b2 is at least one of polysaccharides, polyethyleneimines, polyesters, polyethers, polyamides, polyurethanes, polyureas, or polyimides,
   the crosslinkable polymer b2 has a number-average molecular weight of 1000 or more, and
   the polymer b1 is a graft polymer having the polysiloxane structure in a graft chain, Group I of reactive groups hydroxy group, carboxy group, amino group, isocyanate group, oxazolinyl group, epoxy group, vinyl group, ethynyl group, sulfanyl group, azide group, trialkoxysilyl group, halogenated methyl group, and acid anhydride structure.

2. A laminated material used for a medical lubricating member, the laminated material comprising:
a substrate a; and
a layer b disposed on the substrate a,
wherein the layer b is a layer including a crosslinked body formed from a polymer b1 including a polysiloxane structure and a crosslinkable polymer b2 having at least one reactive group in Group I of reactive groups,
the crosslinkable polymer b2 is at least one of polysaccharides, polyethyleneimines, polyesters, polyethers, polyamides, polyurethanes, polyureas, or polyimides,
the crosslinkable polymer b2 has a number-average molecular weight of 1000 or more, and
the polymer b1 is a graft polymer having the polysiloxane structure in a graft chain, Group I of reactive groups
hydroxy group, carboxy group, amino group, isocyanate group, oxazolinyl group, epoxy group, vinyl group, ethynyl group, sulfanyl group, azide group, trialkoxysilyl group, halogenated methyl group, and acid anhydride structure.

3. The laminated material used for a medical lubricating member according to claim 2, wherein the crosslinkable polymer b2 is at least one of polysaccharides, polyethyleneimines, polyesters, polyethers, polyamides, or polyurethanes.

4. The laminated material used for a medical lubricating member according to claim 2, wherein a content of a constituent component derived from the crosslinkable polymer b2 in the crosslinked body is 30 to 90 mass %.

5. The laminated material used for a medical lubricating member according to claim 2, wherein the layer b has a surface subjected to hydrophilic treatment.

6. The laminated material used for a medical lubricating member according to claim 2, wherein the substrate a is formed of at least one of a urethane resin, a silicone resin, a fluorocarbon resin, an olefin resin, or an acrylic resin.

7. The laminated material used for a medical lubricating member according to claim 2, wherein the substrate a is formed of a silicone resin.

8. The laminated material used for a medical lubricating member according to claim 2, wherein the medical lubricating member is used as a member of a medical device selected from the group consisting of a medical tube, a guide wire, an endoscope, a surgical needle, a surgical suture, forceps, an artificial blood vessel, an artificial heart, and a contact lens.

9. The laminated material used for a medical lubricating member according to claim 2,
wherein the polymer b1 has a structural unit represented by formula (1) below and has at least one of a structural unit represented by formula (2) below, a structural unit represented by formula (3) below, or a structural unit represented by formula (4) below,

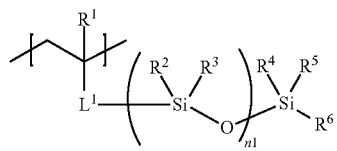

Formula (1)

wherein $R^1$ to $R^6$ represent a hydrogen atom or an organic group, $L^1$ represents a single bond or a divalent linking group, and n1 represents 3 to 10000,

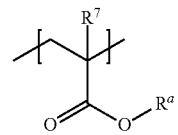

Formula (2)

wherein $R^7$ and $R^a$ represent a hydrogen atom or an organic group,

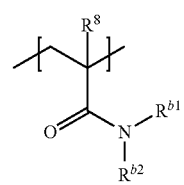

Formula (3)

wherein $R^8$, $R^{b1}$, and $R^{b2}$ represent a hydrogen atom or an organic group, and

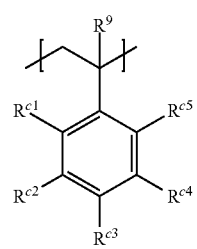

Formula (4)

wherein $R^9$ represents a hydrogen atom or an organic group, and $R^{c1}$ to $R^{c5}$ represent a hydrogen atom, a halogen atom, or an organic group.

10. The laminated material used for a medical lubricating member according to claim 9,
wherein $R^a$ represents a group represented by formula (5) below or a nitrogen-containing organic group,

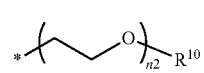

Formula (5)

wherein n2 represents 1 to 10000, $R^{10}$ represents a hydrogen atom or an organic group, and * represents a bonding site.

11. The laminated material used for a medical lubricating member according to claim 9, wherein n1 represents 135 to 10000.

12. A medical lubricating member comprising:
the laminated material used for a medical lubricating member according to claim 2; and
a layer c that is disposed on the layer b constituting the laminated material and that includes a hydrophilic polymer.

13. A medical device comprising:
the medical lubricating member according to claim 12,
wherein the medical device is selected from the group consisting of a medical tube, a guide wire, an endoscope, a surgical needle, a surgical suture, forceps, an artificial blood vessel, an artificial heart, and a contact lens.

\* \* \* \* \*